(12) United States Patent
Butler et al.

(10) Patent No.: US 10,405,883 B2
(45) Date of Patent: Sep. 10, 2019

(54) SURGICAL DEVICE

(71) Applicant: Atropos Limited, County Wicklow (IE)

(72) Inventors: John Butler, County Mayo (IE); Frank Bonadio, County Wicklow (IE); Trevor Vaugh, County Offaly (IE); Ronan Bernard McManus, County Wicklow (IE); Shane Joseph MacNally, County Wicklow (IE); Catherine Deegan, Dublin (IE)

(73) Assignee: Atropos Limited, Bray, County Wicklow (IE)

(*) Notice: Subject to any disclaimer, the term of this patent is extended or adjusted under 35 U.S.C. 154(b) by 218 days.

(21) Appl. No.: 15/658,200

(22) Filed: Jul. 24, 2017

(65) Prior Publication Data
US 2018/0008310 A1    Jan. 11, 2018

Related U.S. Application Data

(63) Continuation of application No. 14/993,781, filed on Jan. 12, 2016, now Pat. No. 9,737,335, which is a continuation of application No. 10/635,910, filed on Aug. 7, 2003, now Pat. No. 9,271,753.

(60) Provisional application No. 60/401,760, filed on Aug. 8, 2002.

(51) Int. Cl.
*A61B 17/34* (2006.01)
*A61B 90/40* (2016.01)
*A61B 17/02* (2006.01)
*A61B 17/00* (2006.01)

(52) U.S. Cl.
CPC ...... *A61B 17/3423* (2013.01); *A61B 17/0293* (2013.01); *A61B 90/40* (2016.02); *A61B 17/3462* (2013.01); *A61B 2017/00265* (2013.01); *A61B 2017/0225* (2013.01); *A61B 2017/3419* (2013.01); *A61B 2017/3429* (2013.01); *A61B 2017/3441* (2013.01); *A61B 2017/3447* (2013.01)

(58) Field of Classification Search
CPC ............ A61B 17/3431; A61B 17/0293; A61B 17/3462
See application file for complete search history.

(56) References Cited

U.S. PATENT DOCUMENTS

| 1,157,202 A | 10/1915 | McLeland |
| 1,598,284 A | 8/1926 | Kinney |
| 1,810,466 A | 6/1931 | Deutsch |

(Continued)

FOREIGN PATENT DOCUMENTS

| DE | 37 39 532 | 12/1988 |
| DE | 37 37 121 | 5/1989 |

(Continued)

OTHER PUBLICATIONS

Kagaya, "Laparoscopic cholecystectomy via two ports, using the "Twin-Port" system", J. Hepatobiliary Pancreat Surg (2001) 8:76-80.

*Primary Examiner* — Andrew Yang
(74) *Attorney, Agent, or Firm* — Bookoff McAndrews, PLLC

(57) ABSTRACT

A seal comprises a first sealing member and a second sealing member. The sealing members each have an accessway to facilitate access from one side of the sealing member to the other side of the sealing member. The accessways are offset to facilitate sealed access of an object through the sealing members.

20 Claims, 42 Drawing Sheets

(56) References Cited

U.S. PATENT DOCUMENTS

| | | |
|---|---|---|
| 2,219,564 A | 10/1940 | Reyniers |
| 2,305,289 A | 12/1942 | Coburg |
| 2,695,608 A | 11/1954 | Gibbon |
| 2,835,253 A | 5/1958 | Borgeson |
| 2,853,075 A | 10/1958 | Hoffman |
| 3,039,468 A | 6/1962 | Price |
| 3,111,943 A | 11/1963 | Orndorff |
| 3,244,169 A | 4/1966 | Baxter |
| 3,253,594 A | 5/1966 | Matthews et al. |
| 3,313,299 A | 4/1967 | Spademan |
| 3,329,390 A | 7/1967 | Hulsey |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 3,402,710 A | 9/1968 | Paleschuck |
| 3,447,533 A | 6/1969 | Spicer |
| 3,522,800 A | 8/1970 | Lesser |
| 3,523,534 A | 8/1970 | Nolan |
| 3,570,475 A | 3/1971 | Weinstein |
| 3,592,198 A | 7/1971 | Evans |
| 3,656,485 A | 4/1972 | Robertson |
| 3,685,786 A | 8/1972 | Woodson |
| 3,717,151 A | 2/1973 | Collett |
| 3,729,006 A | 4/1973 | Wilder et al. |
| 3,782,370 A | 1/1974 | McDonald |
| 3,797,478 A | 3/1974 | Walsh et al. |
| 3,807,393 A | 4/1974 | McDonald |
| 3,828,764 A | 8/1974 | Jones |
| 3,841,332 A | 10/1974 | Treacle |
| 3,853,126 A | 12/1974 | Schulte |
| 3,853,127 A | 12/1974 | Spademan |
| 3,856,021 A | 12/1974 | Macintosh |
| 3,907,389 A | 9/1975 | Cox et al. |
| 3,915,171 A | 10/1975 | Shermeta |
| 3,965,890 A | 6/1976 | Gauthier |
| 3,996,623 A | 12/1976 | Kaster |
| 3,998,217 A | 12/1976 | Trumbull et al. |
| 4,000,739 A | 1/1977 | Stevens |
| 4,016,884 A | 4/1977 | Kwan-Gett |
| 4,024,872 A | 5/1977 | Muldoon |
| 4,030,500 A | 6/1977 | Ronnquist |
| 4,083,370 A | 4/1978 | Taylor |
| 4,096,853 A | 6/1978 | Weigand |
| 4,112,932 A | 9/1978 | Chiulli |
| 4,130,113 A | 12/1978 | Graham |
| 4,177,814 A | 12/1979 | Knepshield |
| 4,188,945 A | 2/1980 | Wenander |
| 4,217,664 A | 8/1980 | Faso |
| 4,228,792 A | 10/1980 | Rhys-Davies |
| 4,239,036 A | 12/1980 | Krieger |
| 4,240,411 A | 12/1980 | Hosono |
| 4,253,201 A | 3/1981 | Ross et al. |
| 4,306,562 A | 12/1981 | Osborne |
| 4,321,915 A | 3/1982 | Leighton |
| 4,331,138 A | 5/1982 | Jessen |
| 4,338,934 A | 7/1982 | Spademan |
| 4,338,937 A | 7/1982 | Lehrman |
| 4,367,728 A | 1/1983 | Mutke |
| 4,399,816 A | 8/1983 | Spangler |
| 4,411,659 A | 10/1983 | Jensen et al. |
| 4,421,296 A | 12/1983 | Stephens |
| 4,424,833 A | 1/1984 | Spector |
| 4,428,364 A | 1/1984 | Bartolo |
| 4,430,081 A | 2/1984 | Timmermans |
| 4,434,791 A | 3/1984 | Darnell |
| 4,436,519 A | 3/1984 | O'Neill |
| 4,485,490 A | 12/1984 | Akers et al. |
| 4,488,877 A | 12/1984 | Klein |
| 4,543,088 A | 9/1985 | Bootman |
| 4,550,713 A | 11/1985 | Hyman |
| 4,553,537 A | 11/1985 | Rosenberg |
| 4,601,710 A | 7/1986 | Moll |
| 4,610,665 A | 9/1986 | Matsumoto |
| 4,626,245 A | 12/1986 | Weinstein |
| 4,634,424 A | 1/1987 | O'Boyle |
| 4,649,904 A | 3/1987 | Krauter |
| 4,654,030 A | 3/1987 | Moll et al. |
| 4,673,393 A | 6/1987 | Suzuki et al. |
| 4,673,394 A | 6/1987 | Fenton |
| 4,755,170 A | 7/1988 | Golden |
| 4,776,843 A | 10/1988 | Martinez et al. |
| 4,777,943 A | 10/1988 | Chvapil |
| 4,784,646 A | 11/1988 | Feingold |
| 4,798,594 A | 1/1989 | Hillstead |
| 4,809,679 A | 3/1989 | Shimonaka |
| 4,863,438 A | 9/1989 | Gauderer |
| 4,889,107 A | 12/1989 | Kaufman |
| 4,895,565 A | 1/1990 | Hillstead |
| 4,897,081 A | 1/1990 | Poirier |
| 4,903,710 A | 2/1990 | Jessamine et al. |
| 4,950,222 A | 8/1990 | Scott et al. |
| 4,950,223 A | 8/1990 | Silvanov |
| 4,984,564 A | 1/1991 | Yuen |
| 4,991,593 A | 2/1991 | LeVahn |
| 4,998,538 A | 3/1991 | Charowsky et al. |
| 5,002,557 A | 3/1991 | Hasson |
| 5,015,228 A | 5/1991 | Columbus et al. |
| 5,019,101 A | 5/1991 | Purkait |
| 5,026,366 A | 6/1991 | Leckrone |
| 5,041,095 A | 8/1991 | Littrell |
| 5,045,070 A | 9/1991 | Grodecki et al. |
| D320,658 S | 10/1991 | Quigley et al. |
| 5,071,411 A | 12/1991 | Hillstead |
| 5,074,878 A | 12/1991 | Bark et al. |
| 5,082,005 A | 1/1992 | Kaldany |
| 5,086,763 A | 2/1992 | Hathman |
| 5,092,846 A | 3/1992 | Nishijima |
| 5,125,897 A | 6/1992 | Quinn et al. |
| 5,129,885 A | 7/1992 | Green et al. |
| 5,141,498 A | 8/1992 | Christian |
| 5,149,327 A | 9/1992 | Oshiyama |
| 5,156,617 A | 10/1992 | Reid |
| 5,158,553 A | 10/1992 | Berry et al. |
| 5,159,921 A | 11/1992 | Hoover |
| 5,161,773 A | 11/1992 | Tower |
| 5,167,636 A | 12/1992 | Clement |
| 5,178,162 A | 1/1993 | Bose |
| 5,188,595 A | 2/1993 | Jacobi |
| 5,192,301 A | 3/1993 | Kamiya et al. |
| 5,197,955 A | 3/1993 | Stephens et al. |
| 5,207,656 A | 5/1993 | Kranys |
| 5,209,737 A | 5/1993 | Richartt |
| 5,211,370 A | 5/1993 | Powers |
| 5,211,633 A | 5/1993 | Strouder |
| 5,213,114 A | 5/1993 | Bailey, Jr. |
| 5,234,455 A | 8/1993 | Mulhollan |
| 5,242,409 A | 9/1993 | Buelna |
| 5,248,304 A | 9/1993 | Vigdorchik et al. |
| 5,261,883 A | 11/1993 | Hood et al. |
| 5,263,922 A | 11/1993 | Sova et al. |
| 5,269,763 A | 12/1993 | Boehmer |
| 5,269,772 A | 12/1993 | Wilk |
| D343,236 S | 1/1994 | Quigley et al. |
| 5,279,575 A | 1/1994 | Sugarbaker |
| D346,022 S | 4/1994 | Quigley et al. |
| 5,299,582 A | 4/1994 | Potts |
| 5,300,036 A | 4/1994 | Mueller |
| 5,308,336 A | 5/1994 | Hart et al. |
| 5,309,896 A | 5/1994 | Moll et al. |
| 5,316,541 A | 5/1994 | Fischer |
| 5,320,611 A | 6/1994 | Bonutti |
| 5,330,437 A | 7/1994 | Durman |
| 5,330,497 A | 7/1994 | Freitas |
| 5,334,143 A | 8/1994 | Carroll |
| 5,336,192 A | 8/1994 | Palestrant |
| 5,342,315 A | 8/1994 | Rowe et al. |
| 5,342,385 A | 8/1994 | Norelli et al. |
| 5,350,364 A | 9/1994 | Stephens et al. |
| 5,364,345 A | 11/1994 | Lowery et al. |
| 5,366,478 A | 11/1994 | Brinkerhoff et al. |
| 5,368,545 A | 11/1994 | Schaller et al. |
| 5,383,861 A | 1/1995 | Hempel |
| 5,385,553 A | 1/1995 | Hart et al. |

(56) References Cited

U.S. PATENT DOCUMENTS

| | | |
|---|---|---|
| 5,391,153 A | 2/1995 | Haber et al. |
| 5,391,156 A | 2/1995 | Hildwein et al. |
| 5,395,367 A | 3/1995 | Wilk |
| 5,403,264 A | 4/1995 | Wohlers |
| 5,407,433 A | 4/1995 | Loomas |
| 5,423,848 A | 6/1995 | Washizuka et al. |
| 5,429,609 A | 7/1995 | Yoon |
| 5,431,676 A | 7/1995 | Durbal |
| 5,443,452 A | 8/1995 | Hart et al. |
| 5,456,284 A | 10/1995 | Ryan |
| 5,476,475 A | 12/1995 | Gadberry |
| 5,480,410 A | 1/1996 | Cuschieri et al. |
| 5,496,280 A | 3/1996 | Vandenbroeck |
| 5,503,112 A | 4/1996 | Luhman |
| 5,514,109 A | 5/1996 | Mollenauer et al. |
| 5,514,133 A | 5/1996 | Golub et al. |
| 5,520,632 A | 5/1996 | Leveen |
| 5,522,791 A | 6/1996 | Leyva |
| 5,522,824 A | 6/1996 | Ashby |
| 5,524,644 A | 6/1996 | Crook |
| 5,526,536 A | 6/1996 | Cartmill |
| 5,545,179 A | 8/1996 | Williamson, IV |
| 5,562,632 A | 10/1996 | Davila |
| 5,562,688 A | 10/1996 | Riza |
| 5,577,993 A | 11/1996 | Zhu et al. |
| 5,582,577 A | 12/1996 | Lund et al. |
| 5,584,850 A | 12/1996 | Hart et al. |
| 5,601,579 A | 2/1997 | Semertzides |
| 5,620,415 A | 4/1997 | Lucey |
| 5,632,979 A | 5/1997 | Goldberg |
| 5,634,911 A | 6/1997 | Hermann et al. |
| 5,634,936 A | 6/1997 | Linden |
| 5,634,937 A | 6/1997 | Mollenauer et al. |
| 5,636,645 A | 6/1997 | Ou |
| 5,640,977 A | 6/1997 | Leahy et al. |
| 5,649,550 A | 7/1997 | Crook |
| 5,653,705 A | 8/1997 | de la Torre et al. |
| 5,657,963 A | 8/1997 | Hinchliffe |
| 5,658,272 A | 8/1997 | Hasson |
| 5,658,306 A | 8/1997 | Kieturakis |
| 5,672,168 A | 9/1997 | de la Torre et al. |
| 5,685,854 A | 11/1997 | Green |
| 5,707,703 A | 1/1998 | Rothrum et al. |
| 5,709,664 A | 1/1998 | Vandenbroeck |
| 5,720,730 A | 2/1998 | Blake, III |
| 5,738,628 A | 4/1998 | Sierocuk et al. |
| 5,741,234 A | 4/1998 | Aboul-Hosn |
| 5,741,298 A | 4/1998 | MacLeod |
| 5,743,884 A | 4/1998 | Hasson et al. |
| 5,749,882 A | 5/1998 | Hart et al. |
| 5,755,660 A | 5/1998 | Tyagi |
| 5,769,783 A | 6/1998 | Fowler |
| 5,769,794 A | 6/1998 | Conlan et al. |
| 5,782,812 A | 7/1998 | Hart et al. |
| 5,795,290 A | 8/1998 | Bridges |
| 5,803,919 A | 9/1998 | Hart et al. |
| 5,803,921 A | 9/1998 | Bonadio |
| 5,807,350 A | 9/1998 | Diaz |
| 5,810,721 A | 9/1998 | Mueller et al. |
| 5,813,409 A | 9/1998 | Leahy et al. |
| 5,814,026 A | 9/1998 | Yoon |
| 5,817,062 A | 10/1998 | Flom |
| 5,820,555 A | 10/1998 | Mueller |
| 5,832,925 A | 11/1998 | Rothrum |
| 5,848,992 A | 12/1998 | Hart et al. |
| 5,853,395 A | 12/1998 | Crook et al. |
| 5,865,728 A | 2/1999 | Moll et al. |
| 5,871,474 A | 2/1999 | Hermann et al. |
| 5,882,344 A | 3/1999 | Strouder |
| 5,899,208 A | 5/1999 | Bonadio |
| 5,904,703 A | 5/1999 | Gilson |
| 5,906,577 A | 5/1999 | Beane et al. |
| 5,916,232 A | 6/1999 | Hart |
| 5,947,922 A | 9/1999 | MacLeod |
| 5,951,467 A | 9/1999 | Picha et al. |
| 5,957,913 A | 9/1999 | de la Torre et al. |
| 5,964,781 A | 10/1999 | Mollenauer et al. |
| 5,993,485 A | 11/1999 | Beckers |
| 5,994,450 A | 11/1999 | Pearce |
| 5,997,515 A | 12/1999 | de la Torre et al. |
| 6,024,736 A | 2/2000 | de la Torre et al. |
| 6,025,067 A | 2/2000 | Fay |
| 6,033,426 A | 3/2000 | Kaji |
| 6,033,428 A | 3/2000 | Sardella |
| 6,036,685 A | 3/2000 | Mueller |
| 6,042,573 A | 3/2000 | Lucey |
| 6,048,309 A | 4/2000 | Flom et al. |
| 6,059,816 A | 5/2000 | Moenning |
| 6,077,288 A | 6/2000 | Shimomura et al. |
| 6,099,506 A | 8/2000 | Macoviak et al. |
| 6,110,154 A | 8/2000 | Shimomura et al. |
| 6,123,689 A | 9/2000 | To |
| 6,142,935 A | 11/2000 | Flom et al. |
| 6,142,936 A | 11/2000 | Beane et al. |
| 6,149,642 A | 11/2000 | Gerhart et al. |
| 6,150,608 A | 11/2000 | Wambeke |
| 6,159,182 A | 12/2000 | Davis |
| 6,162,172 A | 12/2000 | Cosgrove et al. |
| 6,162,196 A | 12/2000 | Hart et al. |
| 6,162,206 A | 12/2000 | Bindokas |
| 6,163,949 A | 12/2000 | Neuenschwander |
| 6,164,279 A | 12/2000 | Tweedle |
| 6,171,282 B1 | 1/2001 | Ragsdale |
| 6,183,486 B1 | 2/2001 | Snow et al. |
| 6,238,373 B1 | 5/2001 | de la Torre et al. |
| 6,254,533 B1 | 7/2001 | Fadem et al. |
| 6,254,534 B1 | 7/2001 | Butler et al. |
| 6,258,065 B1 | 7/2001 | Dennis |
| 6,315,770 B1 | 11/2001 | de la Torre et al. |
| 6,319,246 B1 | 11/2001 | de la Torre et al. |
| 6,322,541 B2 | 11/2001 | West |
| 6,328,730 B1 | 12/2001 | Harkrider, Jr. |
| 6,346,074 B1 | 2/2002 | Roth |
| 6,382,211 B1 | 5/2002 | Crook |
| 6,420,475 B1 | 7/2002 | Chen |
| 6,440,063 B1 | 8/2002 | Beane |
| 6,450,983 B1 | 9/2002 | Rambo |
| 6,454,783 B1 | 9/2002 | Piskun |
| 6,464,686 B1 | 10/2002 | O'Hara et al. |
| 6,485,435 B1 | 11/2002 | Bakal |
| 6,485,467 B1 | 11/2002 | Crook et al. |
| 6,488,620 B1 | 12/2002 | Segermark et al. |
| 6,533,734 B1 | 3/2003 | Corley, III et al. |
| 6,551,270 B1 | 4/2003 | Bimbo et al. |
| 6,554,793 B1 | 4/2003 | Pauker |
| 6,569,119 B1 | 5/2003 | Haberland et al. |
| 6,578,577 B2 | 6/2003 | Bonadio et al. |
| 6,582,364 B2 | 6/2003 | Butler et al. |
| 6,589,167 B1 | 7/2003 | Shimonmura |
| 6,589,211 B1 | 7/2003 | MacLeod |
| 6,607,504 B2 | 8/2003 | Haarala |
| 6,613,952 B2 | 9/2003 | Rambo |
| 6,623,426 B2 | 9/2003 | Bonadio et al. |
| 6,706,050 B1 | 3/2004 | Giannadakis |
| 6,714,298 B2 | 3/2004 | Ryer |
| 6,723,044 B2 | 4/2004 | Pulford |
| 6,793,621 B2 | 9/2004 | Butler et al. |
| 6,796,940 B2 | 9/2004 | Bonadio et al. |
| 6,797,765 B2 | 9/2004 | Pearce |
| 6,814,078 B2 | 11/2004 | Crook |
| 6,814,700 B1 | 11/2004 | Mueller et al. |
| 6,840,951 B2 | 1/2005 | de la Torre et al. |
| 6,846,287 B2 | 1/2005 | Bonadio et al. |
| 6,860,463 B2 | 3/2005 | Hartley |
| 6,866,861 B1 | 3/2005 | Luhman |
| 6,884,253 B1 | 4/2005 | McFarlane |
| 6,902,541 B2 | 6/2005 | McNally et al. |
| 6,908,430 B2 | 6/2005 | Caldwell |
| 6,916,331 B2 | 7/2005 | Mollenauer et al. |
| 6,936,037 B2 | 8/2005 | Bubb |
| 6,939,296 B2 | 9/2005 | Ewers |
| 6,945,932 B1 | 9/2005 | Caldwell et al. |
| 6,958,037 B2 | 10/2005 | Ewers |
| 6,979,324 B2 | 12/2005 | Bybordi |

(56) References Cited

U.S. PATENT DOCUMENTS

| | | |
|---|---|---|
| 7,008,377 B2 | 3/2006 | Beane |
| 7,052,454 B2 | 5/2006 | Taylor |
| 7,081,089 B2 | 7/2006 | Bonadio et al. |
| 7,083,626 B2 | 8/2006 | Hart et al. |
| 7,112,185 B2 | 9/2006 | Hart et al. |
| 7,118,528 B1 | 10/2006 | Piskun |
| 7,153,319 B1 | 12/2006 | Haberland et al. |
| 7,195,590 B2 | 3/2007 | Butler et al. |
| 7,297,106 B2 | 11/2007 | Yamada et al. |
| 7,300,399 B2 | 11/2007 | Bonadio et al. |
| 7,344,547 B2 | 3/2008 | Piskun |
| 7,445,597 B2 | 11/2008 | Butler et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,749,415 B2 | 7/2010 | Brustad et al. |
| 7,753,901 B2 | 7/2010 | Piskun et al. |
| 7,837,612 B2 | 11/2010 | Gill et al. |
| 7,867,164 B2 | 1/2011 | Butler et al. |
| 7,909,760 B2 | 3/2011 | Albrecht et al. |
| 7,998,068 B2 | 8/2011 | Bonadio et al. |
| 8,012,088 B2 | 9/2011 | Butler et al. |
| 8,021,296 B2 | 9/2011 | Bonadio et al. |
| 8,157,817 B2 | 4/2012 | Bonadio et al. |
| 8,187,178 B2 | 5/2012 | Bonadio et al. |
| 8,317,691 B2 | 11/2012 | Bonadio et al. |
| 8,343,047 B2 | 1/2013 | Albrecht et al. |
| 8,375,955 B2 | 2/2013 | Desai et al. |
| 8,475,490 B2 | 7/2013 | Hess et al. |
| 8,485,970 B2 | 7/2013 | Widenhouse et al. |
| 8,518,024 B2 | 8/2013 | Williams et al. |
| 8,657,740 B2 | 2/2014 | Bonadio et al. |
| 8,734,336 B2 | 5/2014 | Bonadio et al. |
| 8,740,785 B2 | 6/2014 | Butler et al. |
| 8,752,553 B2 | 6/2014 | Bonadio et al. |
| 8,876,708 B1 | 11/2014 | Piskun et al. |
| 8,888,693 B2 | 11/2014 | Bonadio et al. |
| 8,961,406 B2 | 2/2015 | Ortiz et al. |
| 8,961,407 B2 | 2/2015 | Widenhouse et al. |
| 8,986,202 B2 | 3/2015 | Butler et al. |
| 9,078,695 B2 | 7/2015 | Hess et al. |
| 9,095,300 B2 | 8/2015 | Bonadio et al. |
| 9,131,835 B2 | 9/2015 | Widenhouse et al. |
| 9,271,753 B2 | 3/2016 | Butler et al. |
| 9,277,908 B2 | 3/2016 | Butler et al. |
| 2001/0037053 A1 | 11/2001 | Bonadio et al. |
| 2001/0039430 A1 | 11/2001 | Dubrul et al. |
| 2001/0047188 A1 | 11/2001 | Bonadio et al. |
| 2002/0002324 A1 | 1/2002 | Mcmanus |
| 2002/0010389 A1 | 1/2002 | Butler et al. |
| 2002/0038077 A1 | 3/2002 | de la Torre et al. |
| 2002/0072762 A1 | 6/2002 | Bonadio et al. |
| 2002/0111536 A1 | 8/2002 | Cuschieri et al. |
| 2003/0028179 A1 | 2/2003 | Piskun |
| 2003/0078478 A1 | 4/2003 | Bonadio et al. |
| 2003/0139756 A1 | 7/2003 | Brustad |
| 2003/0187376 A1 | 10/2003 | Rambo |
| 2003/0192553 A1 | 10/2003 | Rambo |
| 2003/0225392 A1 | 12/2003 | McMichael |
| 2003/0236549 A1 | 12/2003 | Bonadio et al. |
| 2004/0015185 A1 | 1/2004 | Ewers et al. |
| 2004/0024363 A1 | 2/2004 | Goldberg |
| 2004/0049099 A1 | 3/2004 | Ewers et al. |
| 2004/0049100 A1 | 3/2004 | Butler |
| 2004/0068232 A1 | 4/2004 | Hart et al. |
| 2004/0073090 A1 | 4/2004 | Butler |
| 2004/0092795 A1 | 5/2004 | Bonadio et al. |
| 2004/0092796 A1 | 5/2004 | Butler et al. |
| 2004/0093018 A1 | 5/2004 | Johnson |
| 2004/0097793 A1 | 5/2004 | Butler et al. |
| 2004/0106942 A1 | 6/2004 | Taylor |
| 2004/0143158 A1 | 7/2004 | Hart et al. |
| 2004/0154624 A1 | 8/2004 | Bonadio et al. |
| 2004/0215063 A1 | 10/2004 | Bonadio et al. |
| 2004/0230161 A1 | 11/2004 | Zeiner |
| 2004/0249248 A1 | 12/2004 | Bonadio et al. |
| 2004/0260244 A1 | 12/2004 | Piechowicz et al. |
| 2005/0020884 A1 | 1/2005 | Heart et al. |
| 2005/0033246 A1 | 2/2005 | Ahlberg |
| 2005/0059865 A1 | 3/2005 | Kahle |
| 2005/0065475 A1 | 3/2005 | Hart et al. |
| 2005/0065543 A1 | 3/2005 | Kahle |
| 2005/0090713 A1 | 4/2005 | Gozales |
| 2005/0090716 A1 | 4/2005 | Bonadio et al. |
| 2005/0090717 A1 | 4/2005 | Bonadio et al. |
| 2005/0131349 A1 | 6/2005 | Albrecht |
| 2005/0137609 A1 | 6/2005 | Guiraudon |
| 2005/0148823 A1 | 7/2005 | Vaugh et al. |
| 2005/0155611 A1 | 7/2005 | Vaugh et al. |
| 2005/0159647 A1 | 7/2005 | Hart et al. |
| 2005/0192483 A1 | 9/2005 | Bonadio et al. |
| 2005/0192598 A1 | 9/2005 | Johnson |
| 2005/0197537 A1 | 9/2005 | Bonadio et al. |
| 2005/0203346 A1 | 9/2005 | Bonadio et al. |
| 2005/0209510 A1 | 9/2005 | Bonadio et al. |
| 2005/0222582 A1 | 10/2005 | Wenchell |
| 2005/0240082 A1 | 10/2005 | Bonadio et al. |
| 2005/0241647 A1 | 11/2005 | Nguyen |
| 2005/0267419 A1 | 12/2005 | Smith |
| 2005/0277946 A1 | 12/2005 | Greenhalgh |
| 2005/0288558 A1 | 12/2005 | Ewers |
| 2005/0288634 A1 | 12/2005 | O' Herron |
| 2006/0020164 A1 | 1/2006 | Butler et al. |
| 2006/0020241 A1 | 1/2006 | Piskun et al. |
| 2006/0030755 A1 | 2/2006 | Ewers et al. |
| 2006/0041270 A1 | 2/2006 | Lenker |
| 2006/0047284 A1 | 3/2006 | Gresham |
| 2006/0047293 A1 | 3/2006 | Haberland et al. |
| 2006/0106402 A1 | 5/2006 | McLucas |
| 2006/0149137 A1 | 7/2006 | Pingleton et al. |
| 2006/0149306 A1 | 7/2006 | Hart et al. |
| 2006/0161050 A1 | 7/2006 | Butler et al. |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0258899 A1 | 11/2006 | Gill et al. |
| 2006/0264706 A1 | 11/2006 | Piskun |
| 2007/0004968 A1 | 1/2007 | Bonadio et al. |
| 2007/0049966 A1 | 3/2007 | Bonadio et al. |
| 2007/0093695 A1 | 4/2007 | Bonadio et al. |
| 2007/0118175 A1 | 5/2007 | Butler et al. |
| 2007/0185387 A1 | 8/2007 | Albrecht et al. |
| 2007/0203398 A1 | 8/2007 | Bonadio et al. |
| 2007/0255219 A1 | 11/2007 | Vaugh et al. |
| 2007/0287889 A1 | 12/2007 | Mohr |
| 2007/0299387 A1 | 12/2007 | Williams et al. |
| 2008/0027476 A1 | 1/2008 | Piskun |
| 2008/0097162 A1 | 4/2008 | Bonadio et al. |
| 2008/0097163 A1 | 4/2008 | Butler et al. |
| 2008/0255519 A1 | 10/2008 | Piskun et al. |
| 2008/0281161 A1 | 11/2008 | Albrecht et al. |
| 2008/0281162 A1 | 11/2008 | Albrecht et al. |
| 2009/0012477 A1 | 1/2009 | Norton et al. |
| 2009/0036745 A1 | 2/2009 | Bonadio et al. |
| 2009/0069837 A1 | 3/2009 | Bonadio et al. |
| 2009/0093683 A1 | 4/2009 | Richard et al. |
| 2009/0149714 A1 | 6/2009 | Bonadio |
| 2009/0187079 A1 | 7/2009 | Albrecht et al. |
| 2009/0221966 A1 | 9/2009 | Richard |
| 2009/0292176 A1 | 11/2009 | Bonadio et al. |
| 2009/0326330 A1 | 12/2009 | Bonadio et al. |
| 2010/0057121 A1 | 3/2010 | Piskun et al. |
| 2010/0063362 A1 | 3/2010 | Bonadio et al. |
| 2010/0063364 A1 | 3/2010 | Bonadio et al. |
| 2010/0081880 A1 | 4/2010 | Widenhouse et al. |
| 2010/0081881 A1 | 4/2010 | Murray et al. |
| 2010/0113886 A1 | 5/2010 | Piskun et al. |
| 2010/0204548 A1 | 8/2010 | Bonadio et al. |
| 2010/0217087 A1 | 8/2010 | Bonadio et al. |
| 2010/0261972 A1 | 10/2010 | Widenhouse et al. |
| 2010/0274091 A1 | 10/2010 | Rothstein et al. |
| 2010/0274093 A1 | 10/2010 | Shelton, IV |

(56) References Cited

U.S. PATENT DOCUMENTS

| | | |
|---|---|---|
| 2010/0280326 A1 | 11/2010 | Hess et al. |
| 2011/0011410 A1 | 1/2011 | Desai et al. |
| 2011/0071359 A1 | 3/2011 | Bonadio et al. |
| 2011/0092778 A1 | 4/2011 | Butler et al. |
| 2011/0270195 A1 | 11/2011 | Piskun |
| 2012/0016394 A1 | 1/2012 | Bonadio et al. |
| 2012/0022333 A1 | 1/2012 | Main et al. |
| 2012/0029297 A1 | 2/2012 | Bonadio et al. |
| 2012/0095297 A1 | 4/2012 | Dang et al. |
| 2012/0116172 A1 | 5/2012 | Butler et al. |
| 2012/0123214 A1 | 5/2012 | Bonadio et al. |
| 2013/0041231 A1 | 2/2013 | Bonadio et al. |
| 2013/0060093 A1 | 3/2013 | Bonadio et al. |
| 2013/0116509 A1 | 5/2013 | Bonadio et al. |
| 2013/0245373 A1 | 9/2013 | Okoniewski |
| 2014/0107425 A1 | 4/2014 | Bonadio et al. |
| 2014/0303443 A1 | 10/2014 | Bonadio et al. |
| 2014/0323809 A1 | 10/2014 | Bonadio et al. |
| 2015/0148611 A1 | 5/2015 | Bonadio et al. |
| 2015/0272563 A1 | 10/2015 | Butler et al. |
| 2015/0335353 A1 | 11/2015 | Windenhouse et al. |
| 2016/0022257 A1 | 1/2016 | Bonadio et al. |

FOREIGN PATENT DOCUMENTS

| | | |
|---|---|---|
| DE | 296 00 939 | 6/1998 |
| EP | 0113520 | 7/1984 |
| EP | 0142262 | 5/1985 |
| EP | 0537768 | 4/1993 |
| EP | 0950376 | 10/1999 |
| EP | 1118657 | 7/2001 |
| EP | 1312318 | 5/2003 |
| EP | 1593348 | 11/2005 |
| EP | 2168511 | 3/2010 |
| FR | 1456623 | 9/1966 |
| GB | 1151993 | 5/1969 |
| GB | 1355611 | 6/1974 |
| GB | 1372491 | 10/1974 |
| GB | 1379772 | 1/1975 |
| GB | 1400808 | 7/1975 |
| GB | 1407023 | 9/1975 |
| GB | 1496696 | 12/1977 |
| GB | 2071502 | 9/1981 |
| GB | 2255019 | 10/1992 |
| GB | 2275420 | 8/1994 |
| JP | 10-108868 | 4/1998 |
| JP | 11-290327 | 10/1999 |
| JP | 2001-61850 | 3/2001 |
| JP | 2002-28163 | 1/2002 |
| JP | 2004-509659 | 4/2004 |
| JP | 2004-195037 | 7/2004 |
| JP | 2011-98138 | 5/2011 |
| RU | 1342485 | 1/1997 |
| WO | WO 86/06272 | 11/1986 |
| WO | WO 92/11880 | 7/1992 |
| WO | WO 92/21292 | 12/1992 |
| WO | WO 93/05740 | 4/1993 |
| WO | WO 95/05207 | 2/1995 |
| WO | WO 95/07056 | 3/1995 |
| WO | WO 95/22289 | 8/1995 |
| WO | WO 95/24864 | 9/1995 |
| WO | WO 95/27445 | 10/1995 |
| WO | WO 95/27468 | 10/1995 |
| WO | WO 96/36283 | 11/1996 |
| WO | WO 97/32514 | 9/1997 |
| WO | WO 97/32515 | 9/1997 |
| WO | WO 98/35614 | 8/1998 |
| WO | WO 98/48724 | 11/1998 |
| WO | WO 99/03416 | 1/1999 |
| WO | WO 99/25268 | 5/1999 |
| WO | WO 99/29250 | 6/1999 |
| WO | WO 00/32116 | 6/2000 |
| WO | WO 00/32117 | 6/2000 |
| WO | WO 00/32119 | 6/2000 |
| WO | WO 00/32120 | 6/2000 |
| WO | WO 00/35356 | 6/2000 |
| WO | WO 00/54675 | 9/2000 |
| WO | WO 00/54676 | 9/2000 |
| WO | WO 00/54677 | 9/2000 |
| WO | WO 01/08563 | 2/2001 |
| WO | WO 01/08581 | 2/2001 |
| WO | WO 01/26558 | 4/2001 |
| WO | WO 01/91652 | 12/2001 |
| WO | WO 01/91653 | 12/2001 |
| WO | WO 02/17800 A2 | 3/2002 |
| WO | WO 02/34108 A2 | 5/2002 |
| WO | WO 03/026512 A1 | 4/2003 |
| WO | WO 03/034908 A3 | 5/2003 |
| WO | WO 03/061480 A1 | 7/2003 |
| WO | WO 03/103548 A1 | 12/2003 |
| WO | WO 2004/026153 A1 | 4/2004 |
| WO | WO 2004/030547 A1 | 4/2004 |
| WO | WO 2005/009257 A2 | 2/2005 |
| WO | WO 2005/034766 A2 | 4/2005 |
| WO | WO 2005/089661 | 9/2005 |
| WO | WO 2006/040748 A1 | 4/2006 |
| WO | WO 2006/059318 | 8/2006 |
| WO | WO 2008/121294 A1 | 10/2008 |
| WO | WO 2009/035663 A2 | 3/2009 |
| WO | WO 2014/144233 A1 | 9/2014 |

SURGICAL DEVICE

This application is a Continuation of U.S. application Ser. No. 14/993,781, filed on Jan. 12, 2016, now U.S. Pat. No. 9,737,335, which is a Continuation of U.S. application Ser. No. 10/635,910, filed Aug. 7, 2003, now U.S. Pat. No. 9,271,753, which claims the benefit of U.S. Provisional Application No. 60/401,760, filed Aug. 8, 2002, the contents of all of which are incorporated herein by reference in their entireties.

INTRODUCTION

This invention relates to a surgical device. In particular it relates to a surgical device for retracting a wound opening and sealing the retracted wound opening.

STATEMENTS OF INVENTION

According to the invention there is provided a seal comprising a first sealing member and a second sealing member, each sealing member having an accessway to facilitate access from one side of the sealing member to the other side of the sealing member, the accessways being offset to facilitate sealed access of an object through the sealing members.

In one case the accessway comprises an opening in the sealing member. Preferably the opening is located substantially centrally in the sealing member.

In another case the accessway comprises a passageway extending by the sealing member. Preferably the passageway is located substantially at an edge of the sealing member.

In one embodiment at least one sealing member is manipulable to facilitate alignment of the accessways. Preferably the sealing member is at least partially of a flexible material. The sealing member may be at least partially of a resilient material. Ideally the sealing member is of silicone or latex.

In a preferred case the first sealing member is coupled to the second sealing member. Ideally the seal comprises a ring to which both the first sealing member and the second sealing member are coupled.

The seal may comprise means to bias the first sealing member and the second sealing member towards one another. Preferably the biasing means comprises a magnet coupled to each sealing member.

The seal may comprise three or more sealing members.

Desirably the sealing member comprises a sheet.

In another aspect the invention provides a seal comprising a first sealing member and a second sealing member, each sealing member having an accessway to facilitate access from one side of the sealing member to the other side of the sealing member, and a closure member movable between a sealing position in which the closure member occludes at least one accessway and an access position in which the accessways are at least partially open for passage of an object therethrough.

In one embodiment the seal comprises means to bias the closure member towards the sealing position. Preferably the biasing means comprises one or more resilient members. Ideally the resilient member comprises an elastic band.

The closure member may be located between the first sealing member and the second sealing member. Ideally the seal comprises at least one tether to prevent passage of the closure member through the accessway.

In a preferred embodiment the first sealing member is coupled to the second sealing member. Ideally the seal comprises a ring to which both the first sealing member and the second sealing member are coupled.

The accessway in the first sealing member and the accessway in the second sealing member are preferably aligned. The accessway may comprise an opening in the sealing member. Ideally the opening is located substantially centrally in the sealing member.

In one case the sealing member comprises a collar around the opening. Preferably the collar is provided on a side of the sealing member opposite to the closure member.

Desirably the closure member comprises a ball. The ball may be spherical.

The sealing member preferably comprises a sheet.

The invention also provides a further aspect a seal comprising a first sealing member and a second sealing member, the sealing members being configured to overlap one another such that a portion of the first sealing member overlaps a portion of the second sealing member along a first overlap region and a portion of the second sealing member overlaps a portion of the first sealing member along a second overlap region.

In one embodiment at least one sealing member is manipulable to facilitate sealed passage of an object between the sealing members. Preferably the sealing member is manipulable to facilitate sealed passage at the junction of the first overlap region and the second overlap region. Ideally the sealing member is at least partially of a flexible material. Most Preferably the sealing member is at least partially of a resilient material. The sealing member may be of silicone or latex.

In another embodiment the area of the first overlap region is substantially equal to the area of the second overlap region.

The first sealing member is preferably coupled to the second sealing member. Ideally the seal comprises a ring to which both the first sealing member and the second sealing member are coupled.

The sealing member may comprise a sheet.

In another aspect of the invention there is provided a seal comprising a sleeve through which an object may be passed, and means to bias the sleeve into a closed configuration. The biasing means may be provided integral with the sleeve.

Ideally the sleeve is configured to curl-up upon itself to the closed configuration.

The sleeve may alternatively be configured to twist-up upon itself to the closed configuration.

In one case the seal comprises a platform to which the sleeve is coupled. The platform is preferably of an annular shape. Ideally the platform comprises a stiffening ring.

The invention also provides a surgical device comprising a seal of the invention In another aspect the invention provides a surgical device comprising a proximal seal and a distal seal, the distal seal comprising a seal of the invention.

The proximal seal may comprise a lip seal, or an iris valve.

According to another aspect the invention provides a surgical assembly comprising a surgical device of the invention and a wound retractor.

In one embodiment the device is releasably mountable to the retractor.

In another embodiment the device is integral with the retractor.

The invention also provides in another aspect a surgical device comprising:—
  a retracting member movable from an insertion configuration to a retracting configuration to retract laterally a wound opening; and
  a sealing member for sealing a retracted wound opening; the sealing member having at least two accessways to facilitate sealed access through a retracted wound opening.

In one embodiment of the invention the sealing member comprises at least one chamber for receiving pressurised fluid to seal at least one accessway.

Preferably the sealing member comprises at least one iris valve to seal at least one accessway.

The sealing member may comprise at least one lip seal to seal at least one accessway.

The sealing member is preferably rotatable in a sealed manner relative to the retracting member.

In another aspect the invention provides a surgical device comprising:—
  a retracting member movable from an insertion configuration to a retracting configuration to retract laterally a wound opening; and
  a sealing member for sealing a retracted wound opening; the sealing member being rotatable in a sealed manner relative to the retracting member.

In one case the sealing member is releasably mounted to the retracting member.

The device may comprise a proximal member for location externally of a wound opening, the proximal member being movable relative to the retracting member to move the retracting member to the retracting configuration. Preferably the proximal member comprises an annular ring means. Ideally the annular ring means comprises an inner ring and an outer ring between which the retracting member may be led.

The sealing member may be at least partially transparent.

BRIEF DESCRIPTION OF THE DRAWINGS

The invention will be more clearly understood from the following description of some embodiments thereof, given by way of example only, with reference to the accompanying drawings, in which:—

DETAILED DESCRIPTION

Figure 1:
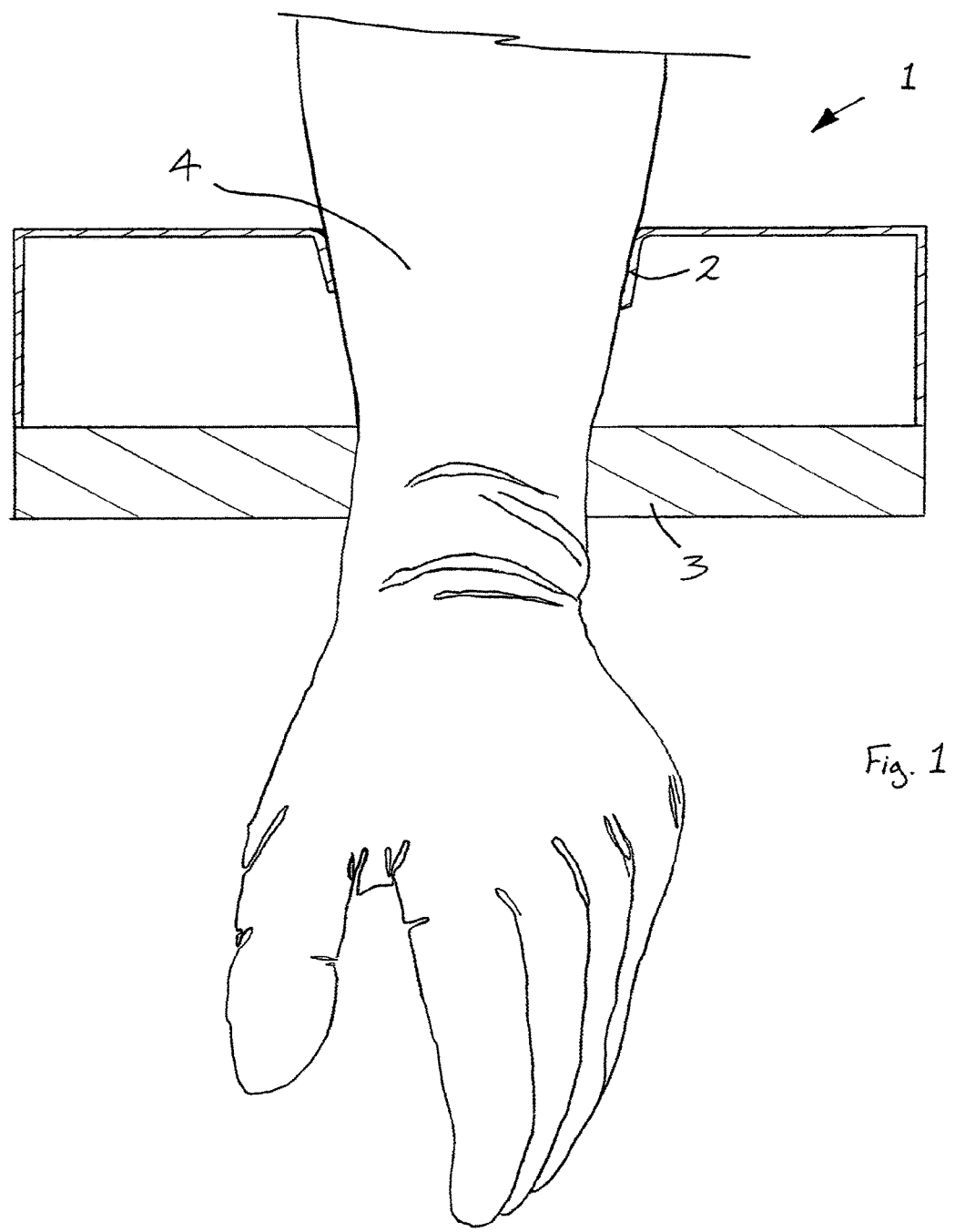
FIG. 1 is a partially cross-sectional, front view of a surgical device according to the invention, in use.

Referring to FIG. 1 there is illustrated a surgical device 1 according to the invention. The device 1 has a proximal seal 2 which is normally open, and a distal seal 3 which is normally closed. This dual seal arrangement facilitates passage of an object, such as a surgeon's forearm 4, through the device 1 into a body cavity in a sealed manner. The surgical device 1 may thus be used to maintain pneumoperitoneum during hand-assisted laparoscopic surgery.

In this case, the proximal seal 2 is provided in the form of a lip seal.

FIGS. 2 to 5 illustrate the distal seal 3 in further detail. The distal seal 3 comprises three sealing members 5, 6, 7. In this case, each sealing member 5, 6, 7 is provided in the form of a sheet coupled to a circumferentially extending O-ring 8.

Each sealing member 5, 6, 7 has an accessway 9, 10, 11 respectively to facilitate access from one side of the sealing member to the other side of the sealing member. The accessways 9, 11 are provided in the form of circular openings through the sealing members 5, 7 located centrally in the sealing members 5, 7. The accessway 10 is provided in the form of a crescent-shaped passageway at the edge of the sealing member 6.

Figure 2:
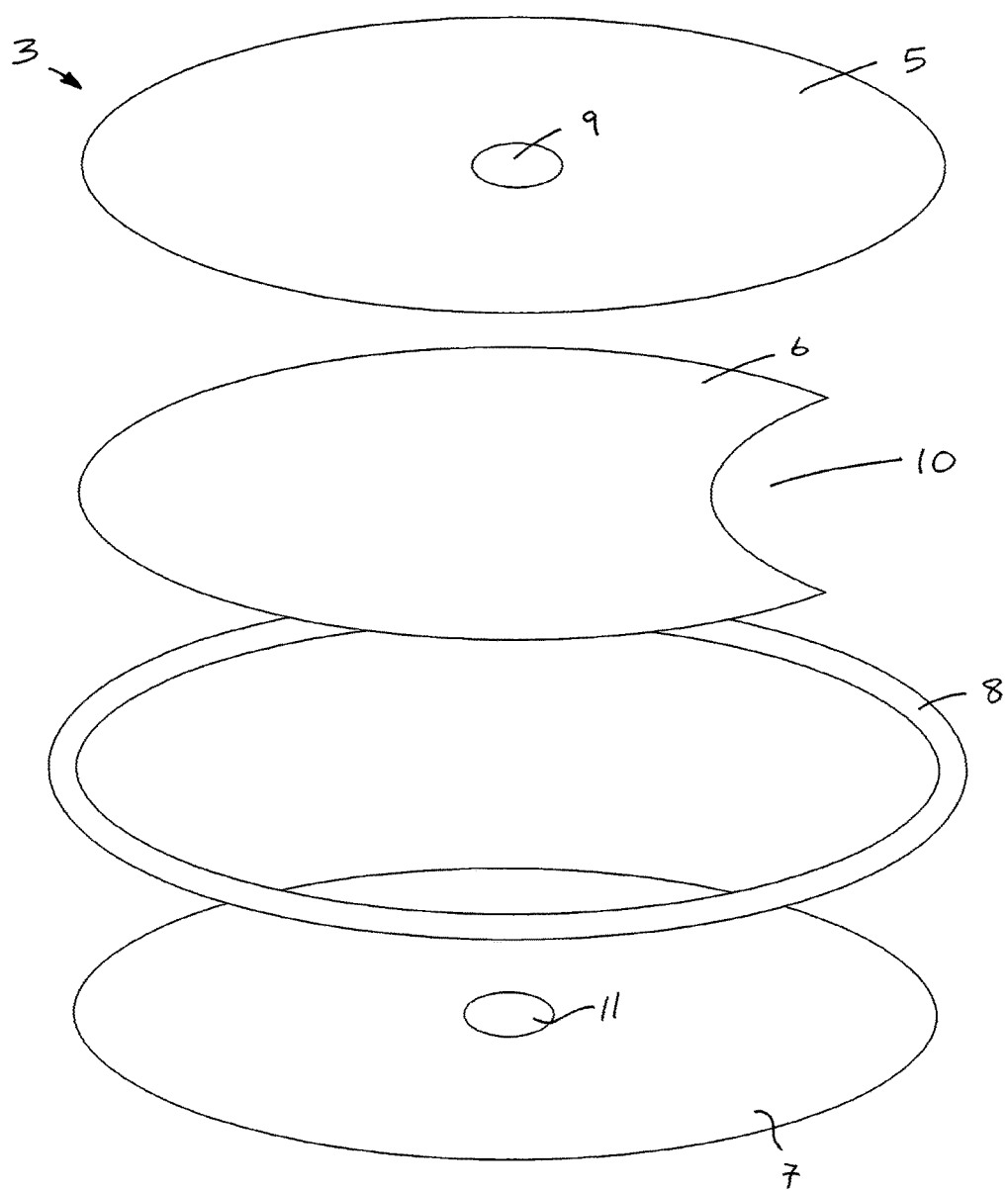
FIG. 2 is an exploded, perspective view of a seal of the device of FIG. 1.
Figure 3:
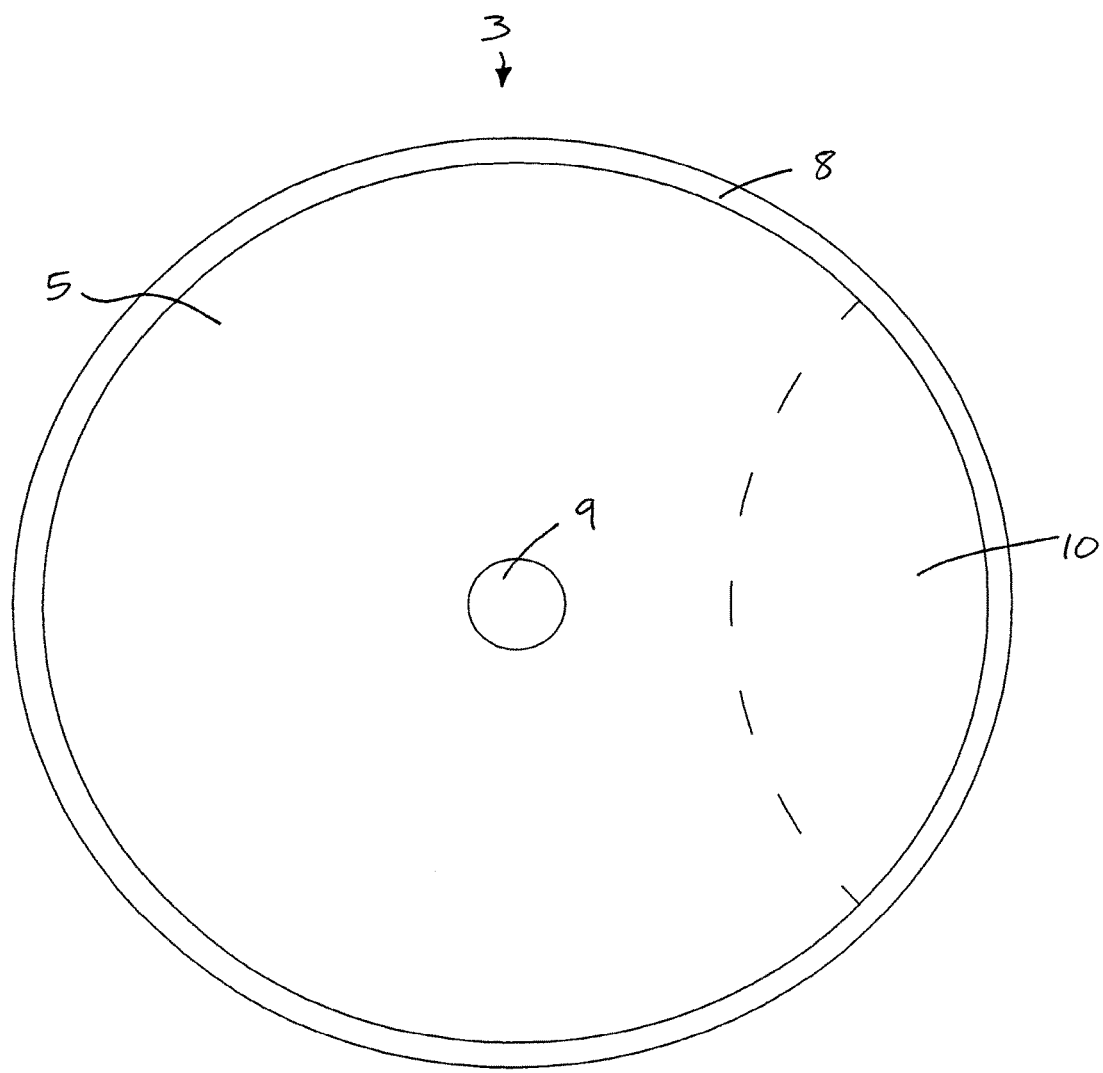
FIG. 3 is a plan view of the seal of FIG. 2.

As illustrated in FIG. 2, the opening 9 is offset from the passageway 10, and the passageway 10 is offset from the opening 11. In this manner the sealing members 5, 6, 7 are normally closed to prevent leakage of insufflation gas through the distal seal 3.

Figure 4:
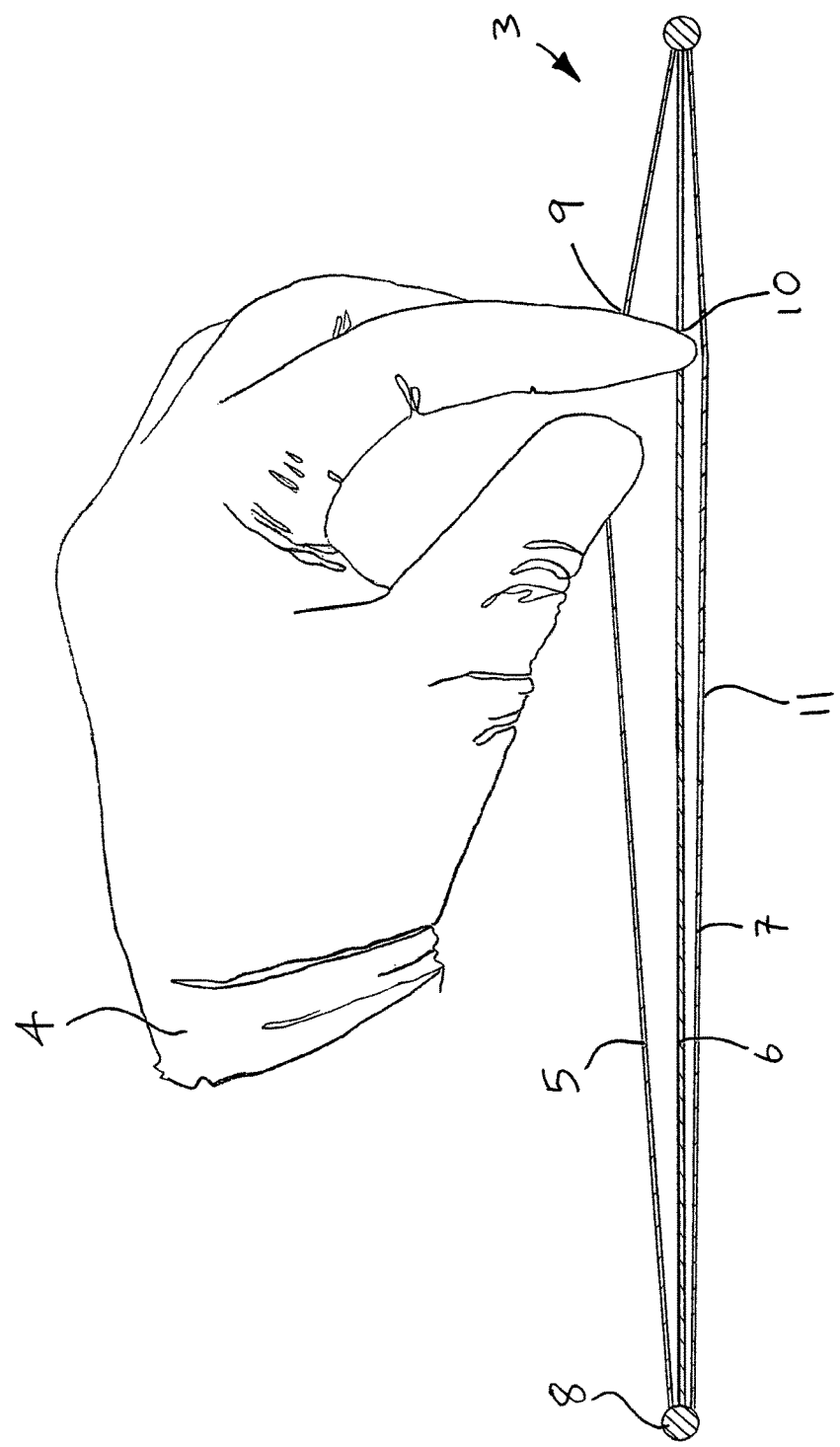
FIGS. 4 and 5 are partially cross-sectional, front views of the seal of FIG. 2, in use.
Figure 5:
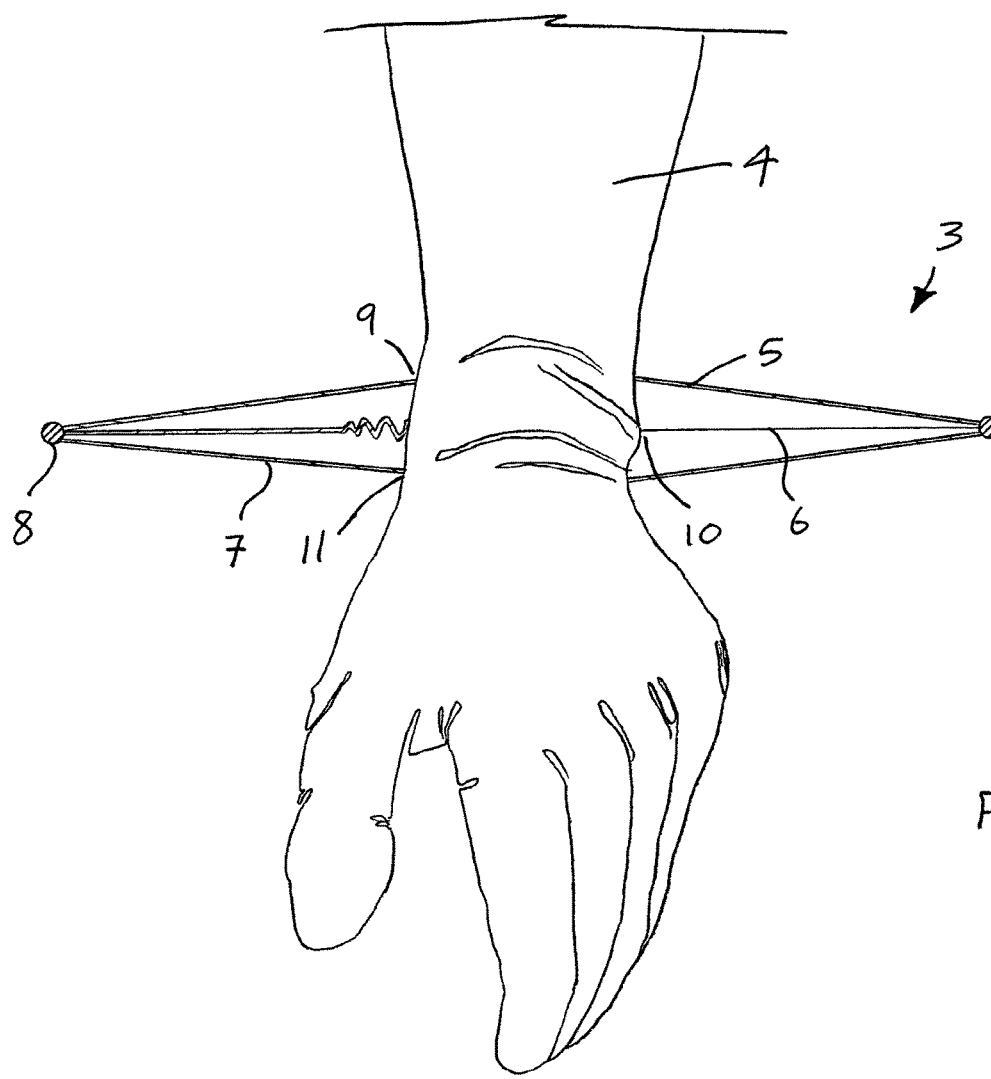

The sealing members 5, 6, 7 are manipulable to facilitate alignment of the accessways 9, 10, 11, as illustrated in FIG. 4. When the accessways 9, 10, 11 have been aligned, the surgeon's hand and arm 4 may be passed through the distal seal 3 to gain access to an internal body cavity and/or internal body organs, as illustrated in FIG. 5.

A suitable material for the sealing members 5, 6, 7 to enable manipulation of the sealing members 5, 6, 7 is a flexible material, such as silicone or latex. The sealing members 5, 6, 7 are preferably also of a resilient material to ensure that the sealing members 5, 6, 7 return to the normally closed position after withdrawal of the surgeon's arm 4.

Figure 6:
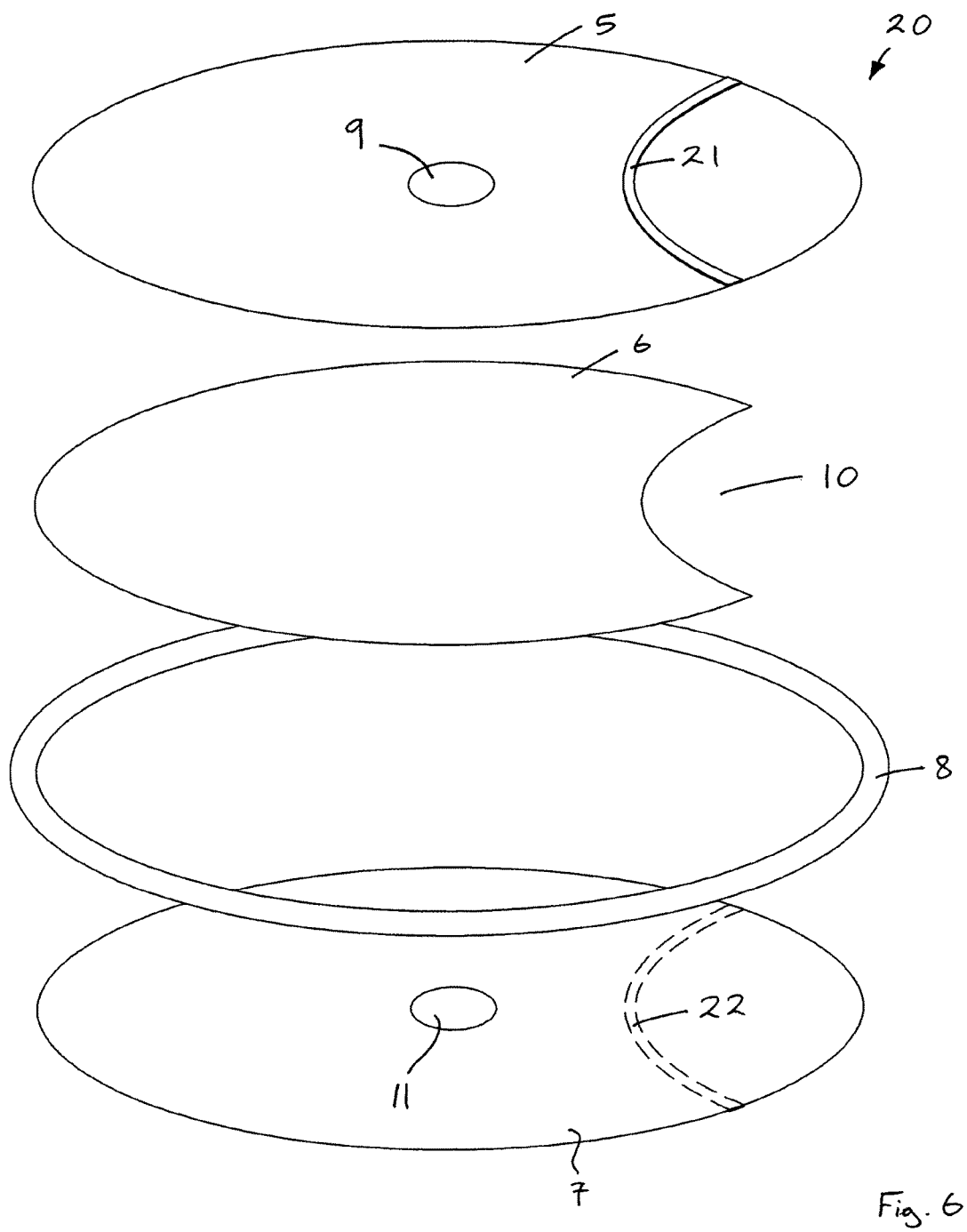
FIGS. 6 and 7 are views similar to FIGS. 2 and 3 of another seal according to the invention.
Figure 7:
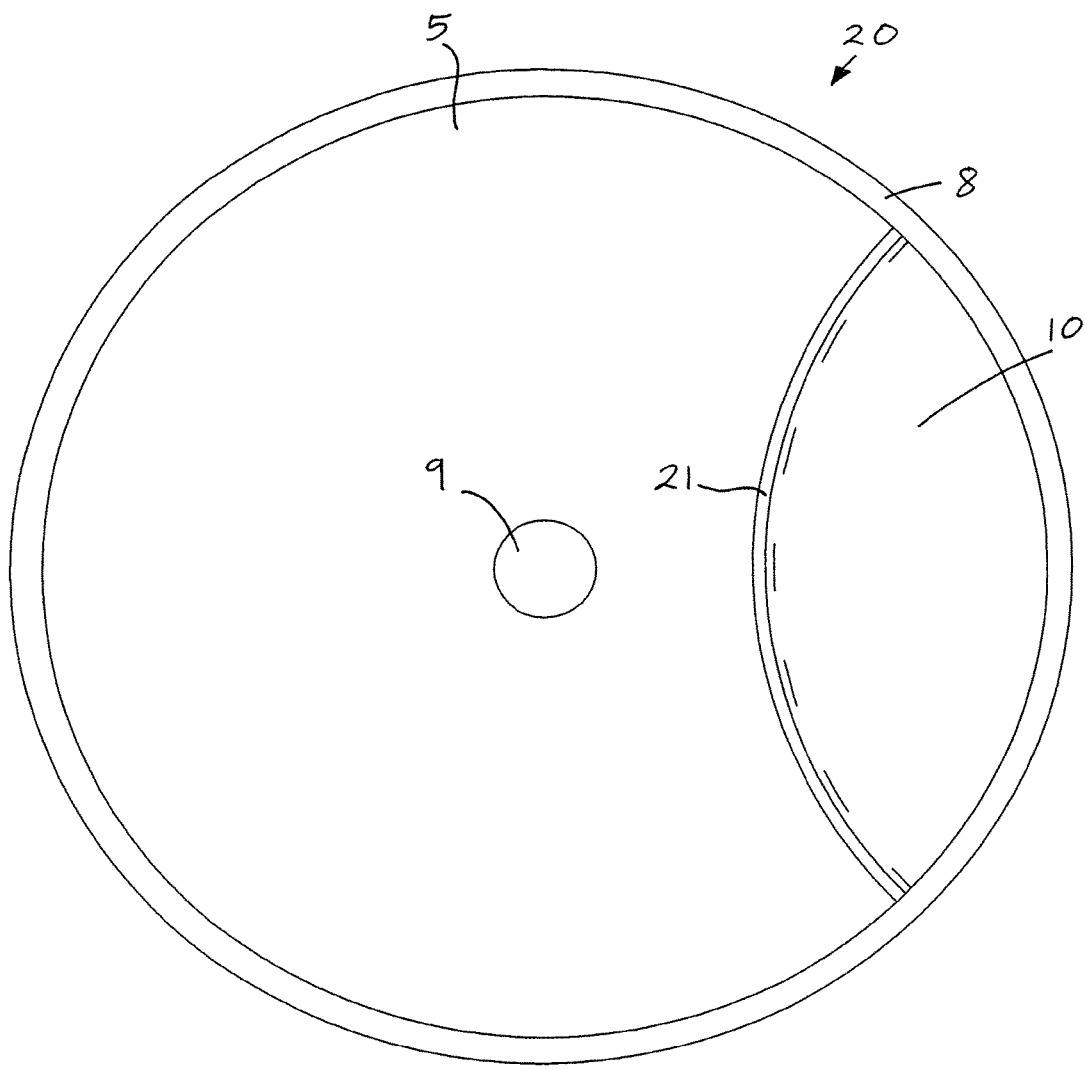
Figure 8:
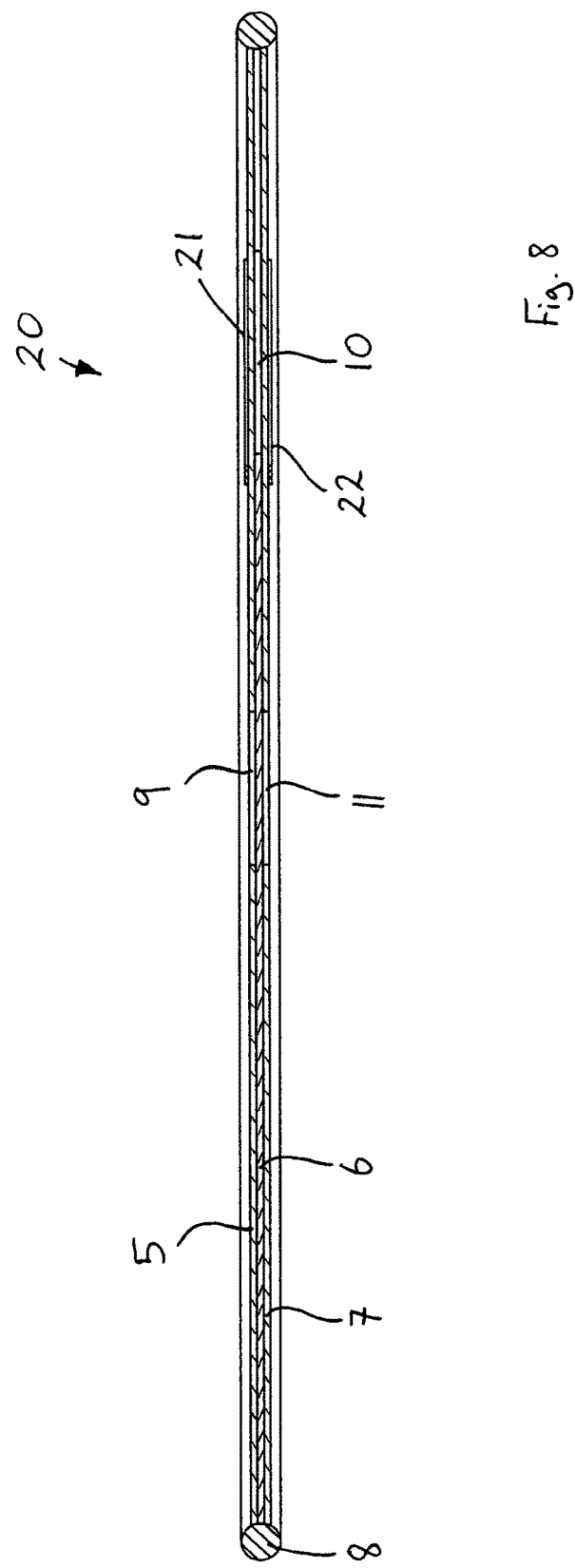
FIG. 8 is a cross-sectional, front view of the seal of FIGS. 6 and 7.
Figure 9:
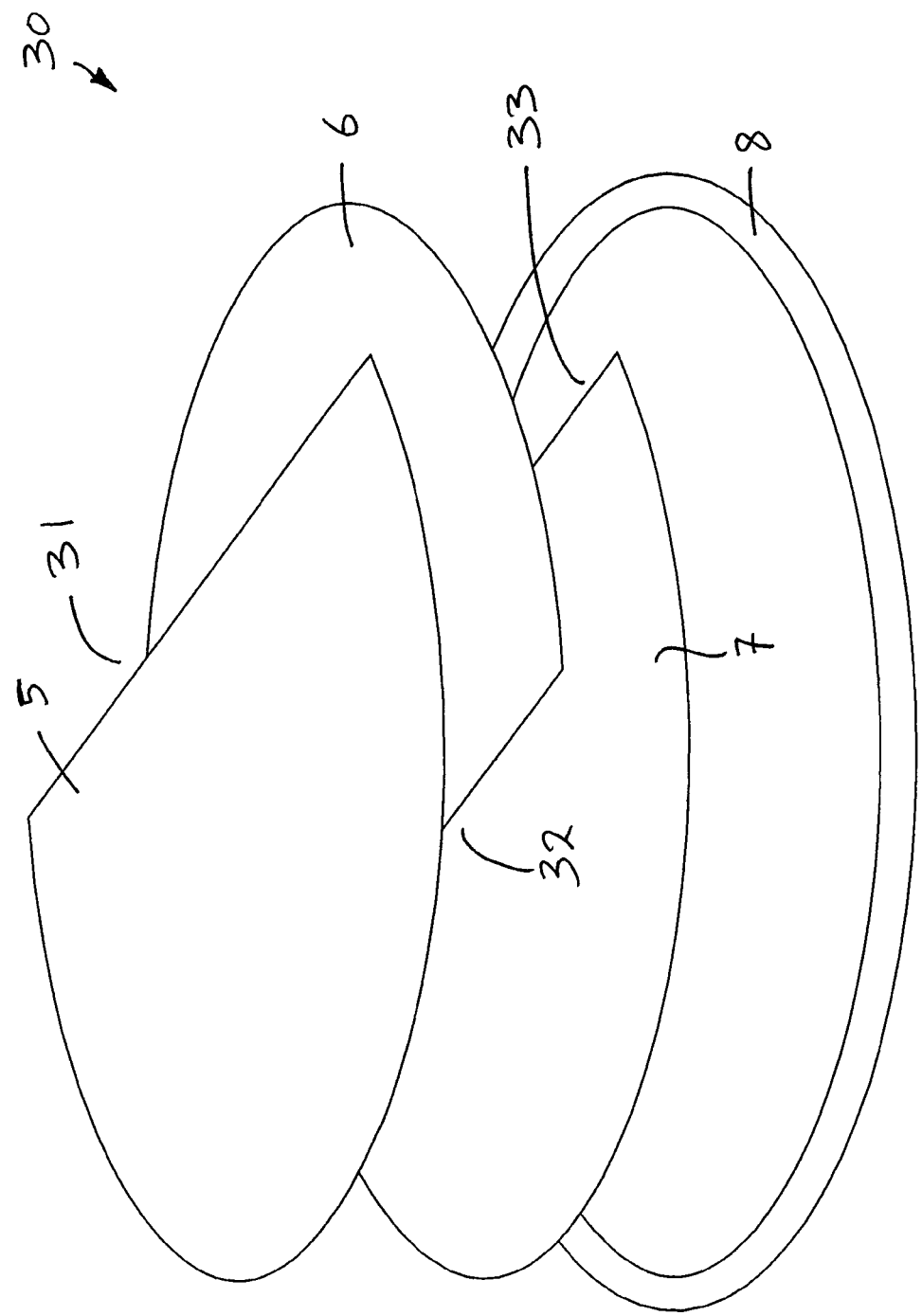
FIGS. 9 to 11 are views similar to FIGS. 6 to 8 of another seal according to the invention.
Figure 10:
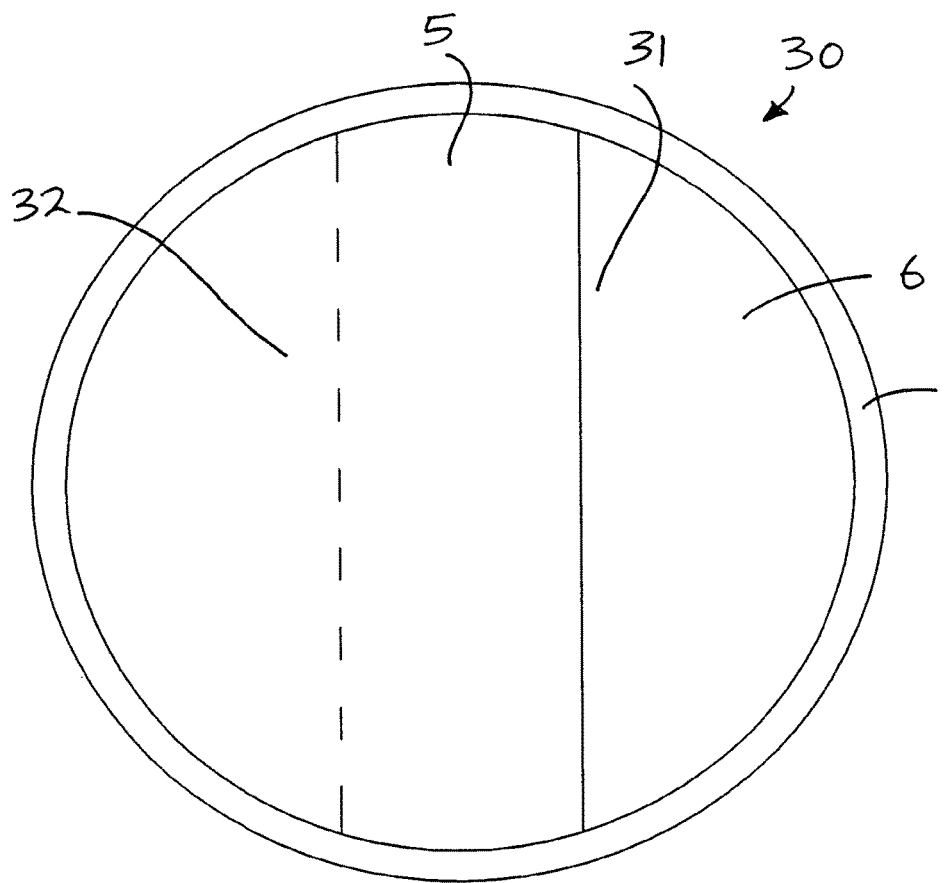
Figure 11:
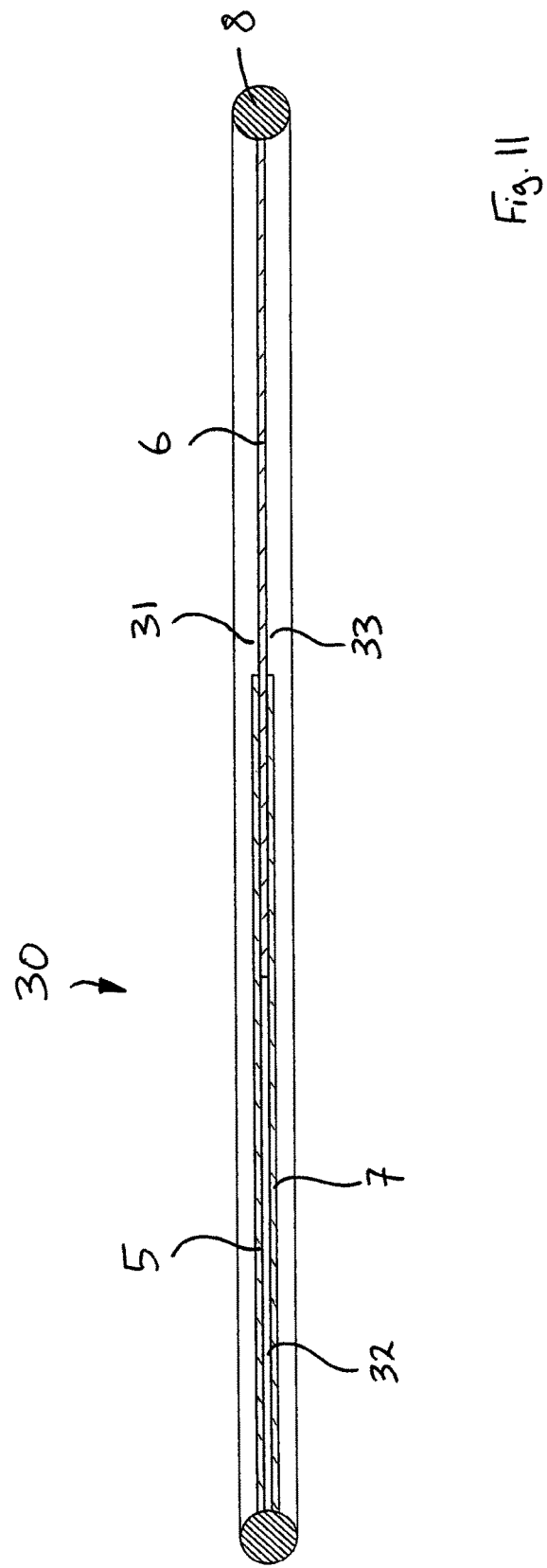
Figure 12:
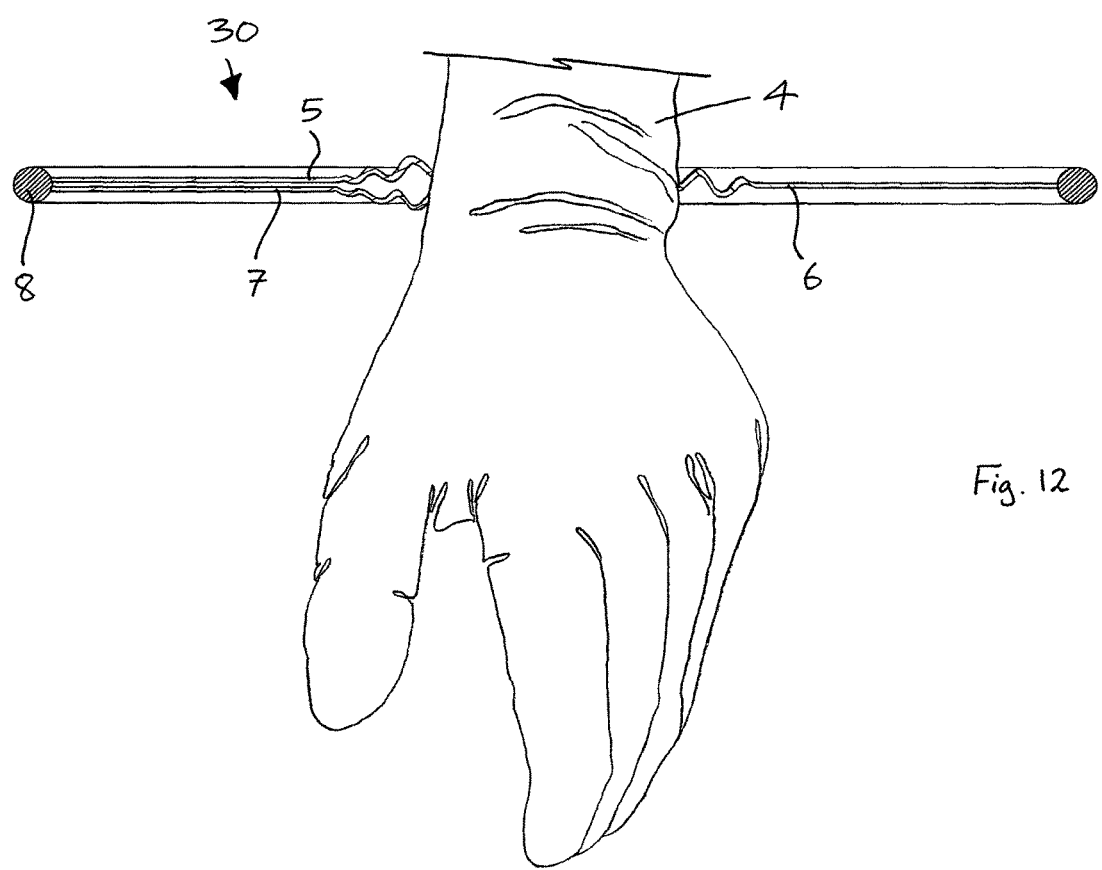
FIG. 12 is a partially cross-sectional, front view of the seal of FIGS. 9 to 11, in use.

In FIGS. 6 to 8 there is illustrated another distal seal 20 according to the invention, which is similar to the distal seal 3 of FIGS. 1 to 5, and similar elements in FIGS. 6 to 8 are assigned the same reference numerals.

In this case the distal seal 20 comprises an arcuate magnet 21 coupled to a proximal surface of the proximal sealing member 5, and an arcuate magnet 22 coupled to a distal surface of the distal sealing member 7. The magnets 21, 22 act to bias the sealing members 5, 7 towards one another with the middle sealing member 6 sandwiched in between. This magnetic arrangement enhances the gas-tight seal achieved by the distal seal 20.

Referring to FIGS. 9 to 12 there is illustrated another distal seal 30 according to the invention, which is similar to the distal seal 3 of FIGS. 1 to 5, and similar elements in FIGS. 9 to 12 are assigned the same reference numerals.

In this case, each accessway 31, 32, 33 is provided in the form of a passageway at the edge of the sealing member 5, 6, 7 respectively. The middle passageway 32 is offset from the proximal and distal passageways 31, 33 respectively. In this manner the sealing members 5, 6, 7 are normally closed to prevent leakage of insufflation gas through the distal seal 30.

Use of the distal seal 30 proceeds in a manner similar to that described previously with reference to the distal seal 3 of FIGS. 1 to 5.

Figure 13:
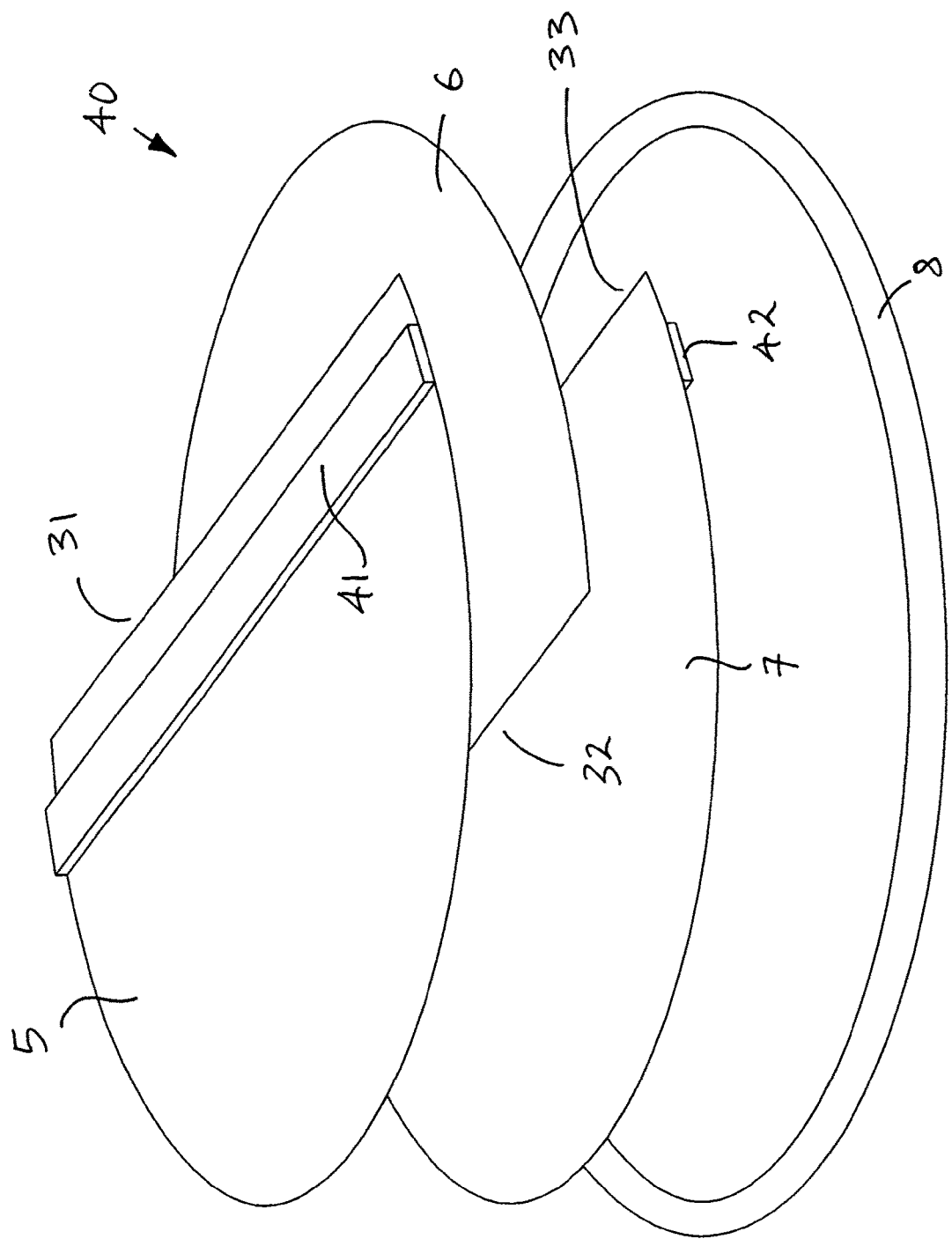
FIGS. 13 and 14 are views similar to FIGS. 9 and 11 of another seal according to the invention.
Figure 14:
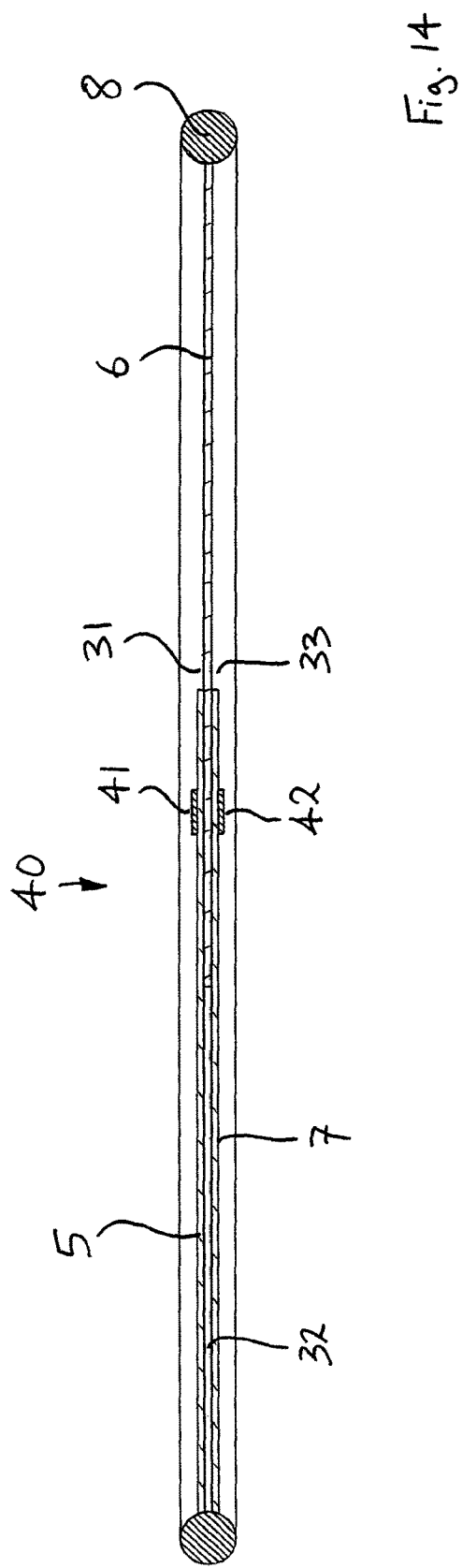

FIGS. 13 and 14 illustrate a further distal seal 40 according to the invention, which is similar to the distal seal 30 of FIGS. 9 to 12, and similar elements in FIGS. 13 and 14 are assigned the same reference numerals.

The distal seal 40 comprises a magnet 41 coupled to the proximal surface of the proximal sealing member 5, and a magnet 42 coupled to the distal surface of the distal sealing member 7, in a manner similar to that described previously with reference to the distal seal 20 of FIGS. 6 to 8.

Referring to FIGS. 15 to 20 there is illustrated another distal seal 50 according to the invention which is suitable for use with the surgical device 1.

The distal seal 50 comprises two sealing members 51, 52 and a spherical ball 56. In this case each sealing member 51, 52 is provided in the form of a sheet coupled to a circumferentially extending O-ring 53.

Figure 15:
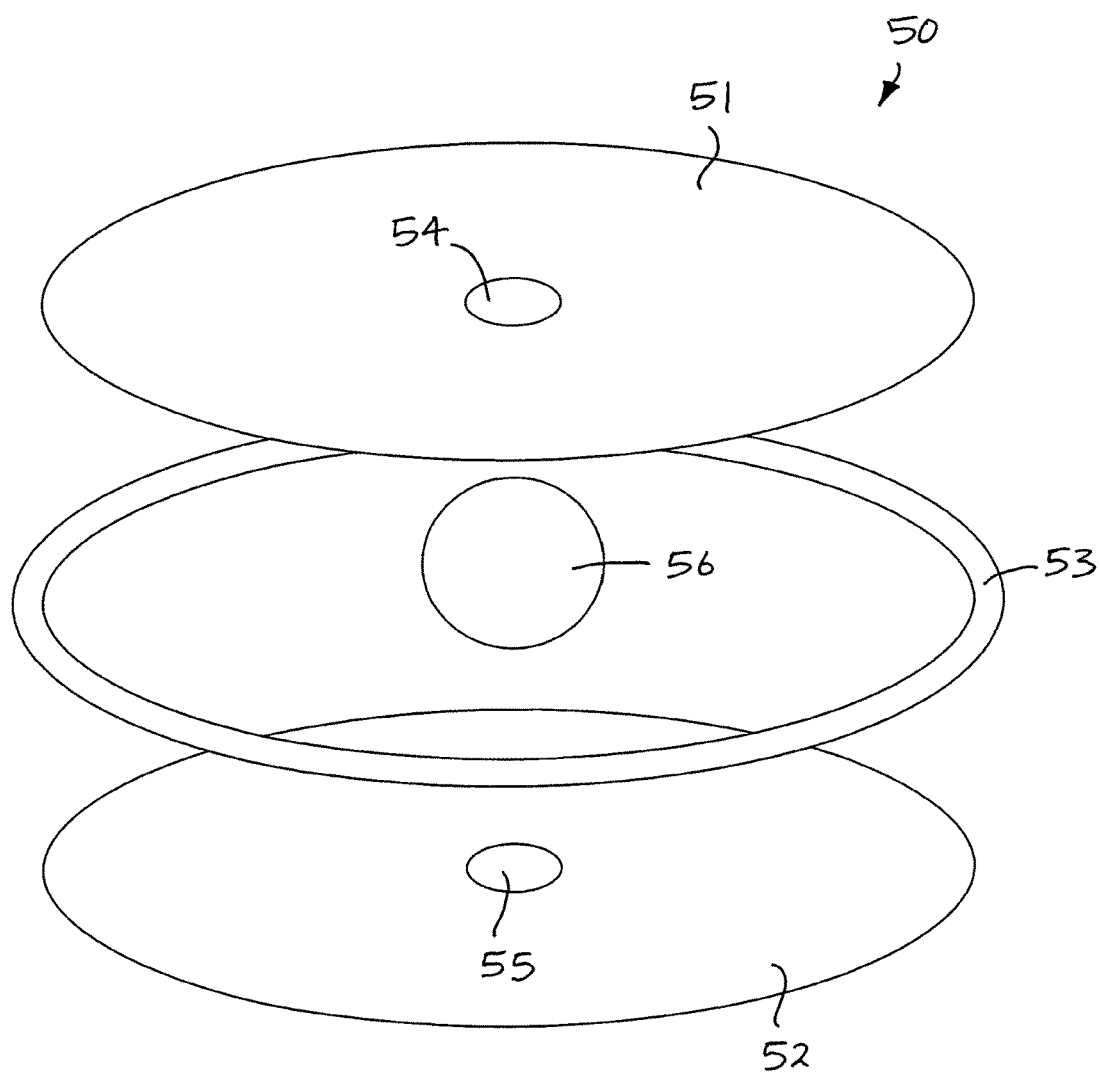
FIGS. 15 to 17 are views similar to FIGS. 6 to 8 of another seal according to the invention.
Figure 16:
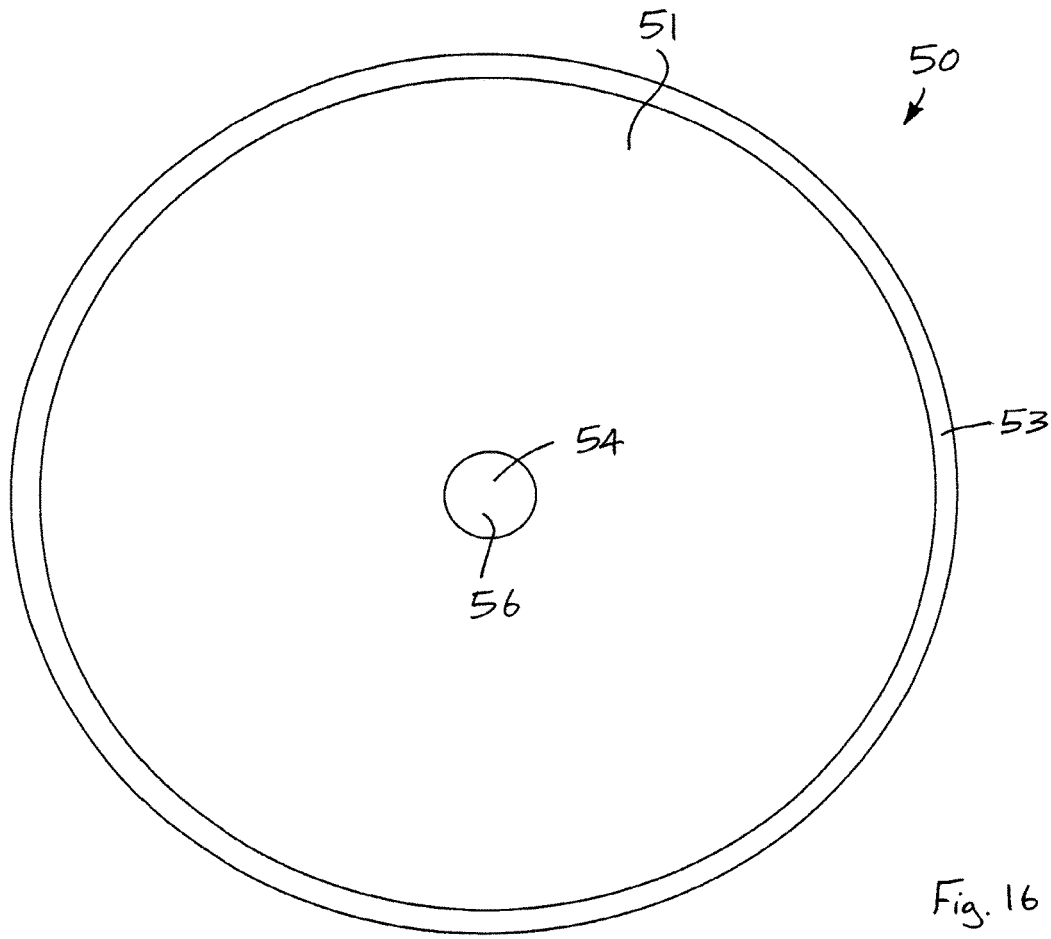

Each sealing member 51, 52 has an accessway 54, 55 respectively to facilitate access from one side of the sealing member to the other side of the sealing member. The accessways 54, 55 are provided in the form of circular openings through the sealing members 51, 52 located centrally in the sealing members 51, 52. As illustrated in FIGS. 15 and 16, the accessways 54, 55 are aligned.

Figure 17:
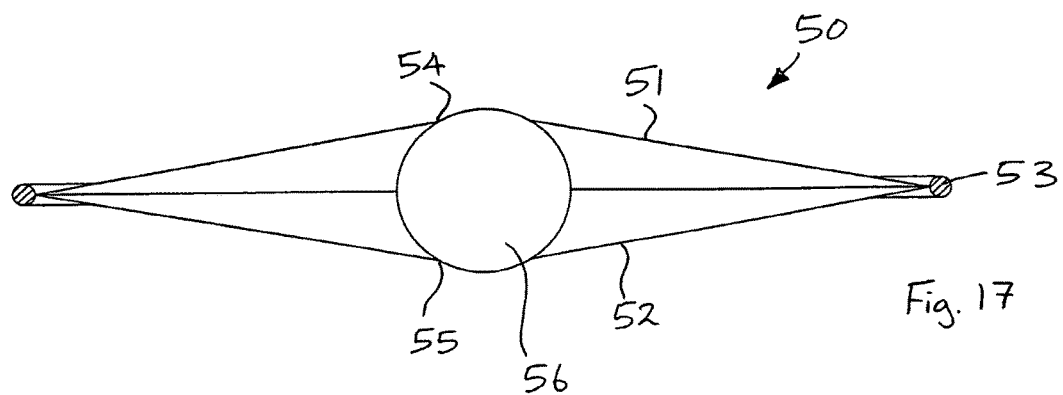
Figure 18:
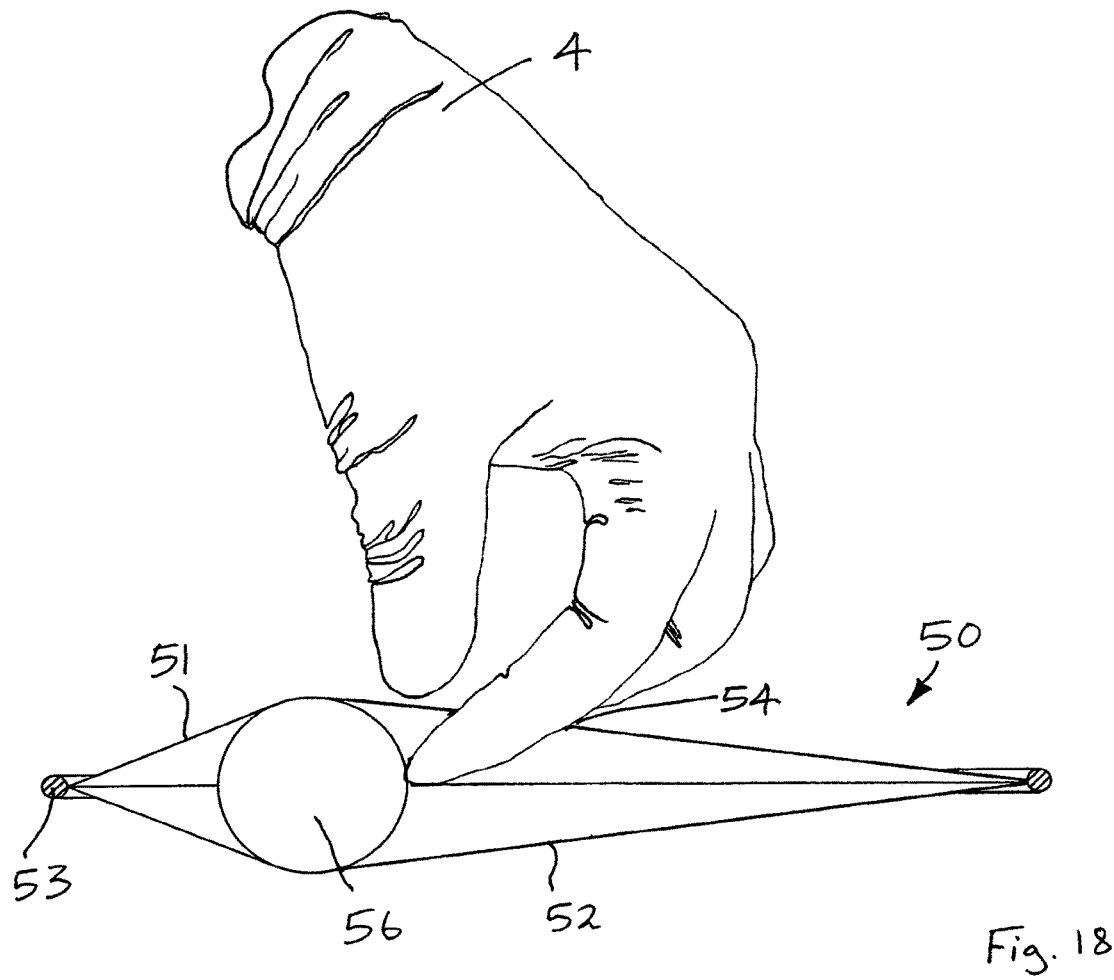
FIGS. 18 to 20 are partially cross-sectional, front views of the seal of FIGS. 15 to 17, in use.
Figure 19:
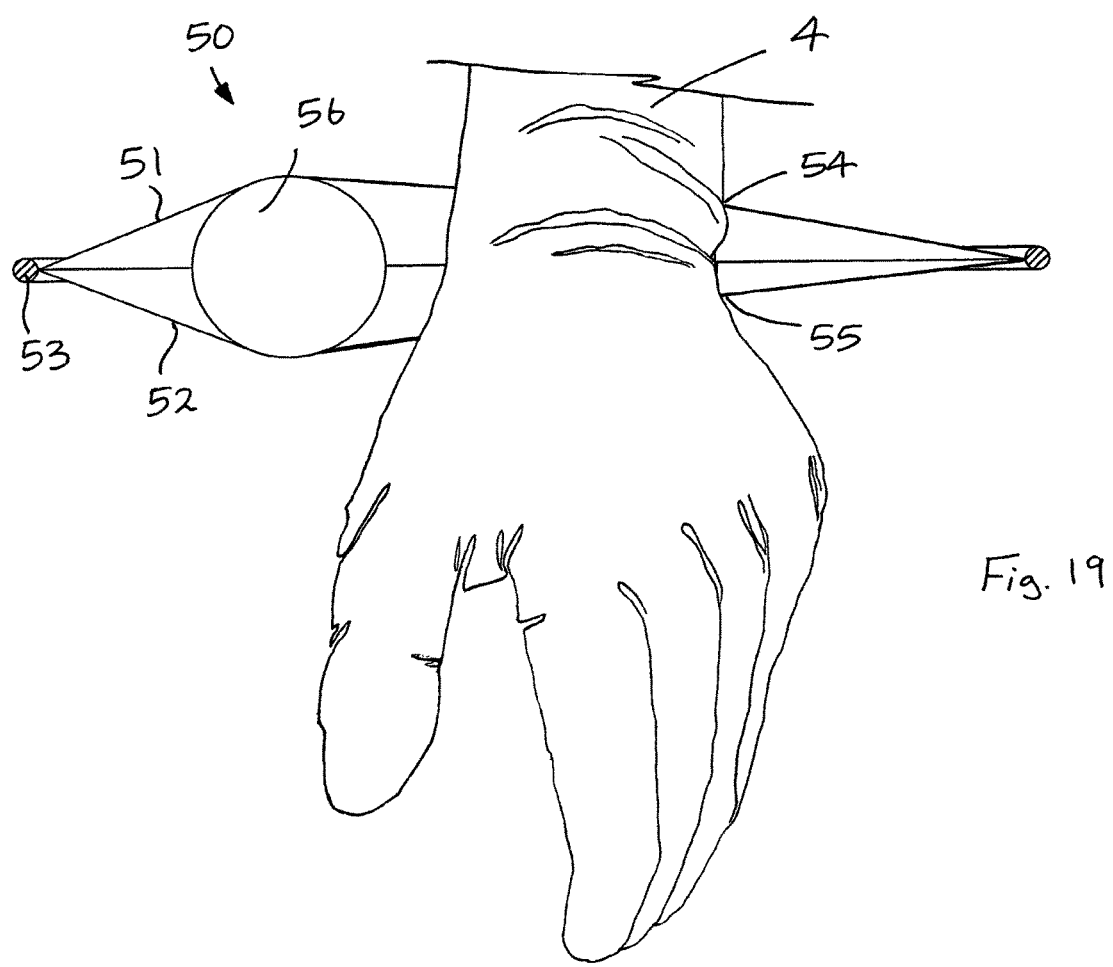
Figure 20:
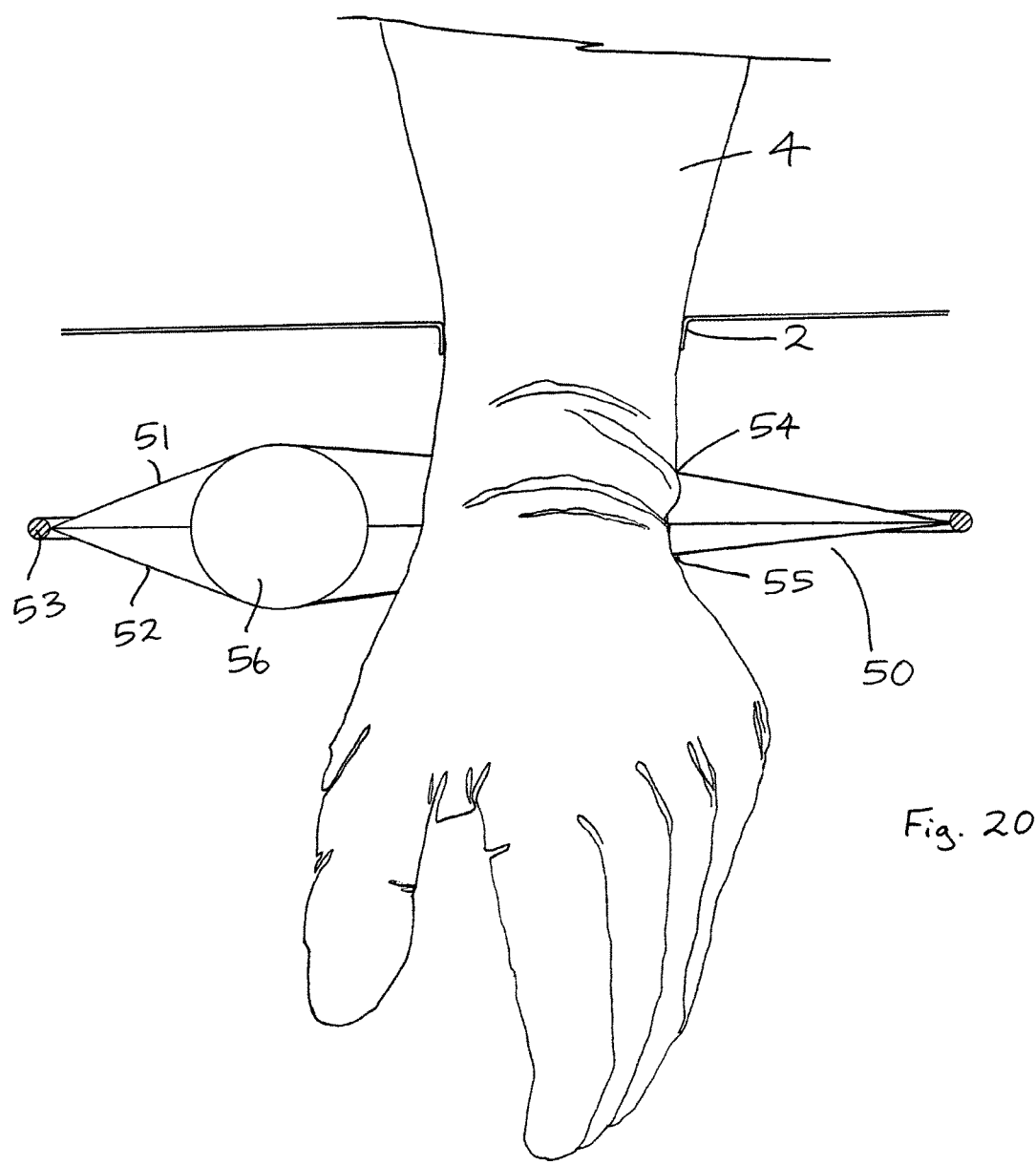

The ball 56 is located between the two sealing members 51, 52, as illustrated in FIG. 17. As illustrated in FIG. 18, the ball 56 is movable laterally within the two sealing members 51, 52 from a sealing position in which the ball 56 occludes the two accessways 54, 55 (FIG. 17), to an access position in which the accessways 54, 55 are open for passage of the surgeon's arm 4 therethrough (FIGS. 19 and 20).

When the ball 56 is in the sealing position (FIG. 17), the distal seal 50 prevents escape of insufflation gas from a body cavity. When the ball 56 is in the access position (FIGS. 19 and 20), the distal seal 50 facilitates sealed access of the surgeon's arm 4 through the distal seal 50 to the body cavity.

Figure 21:
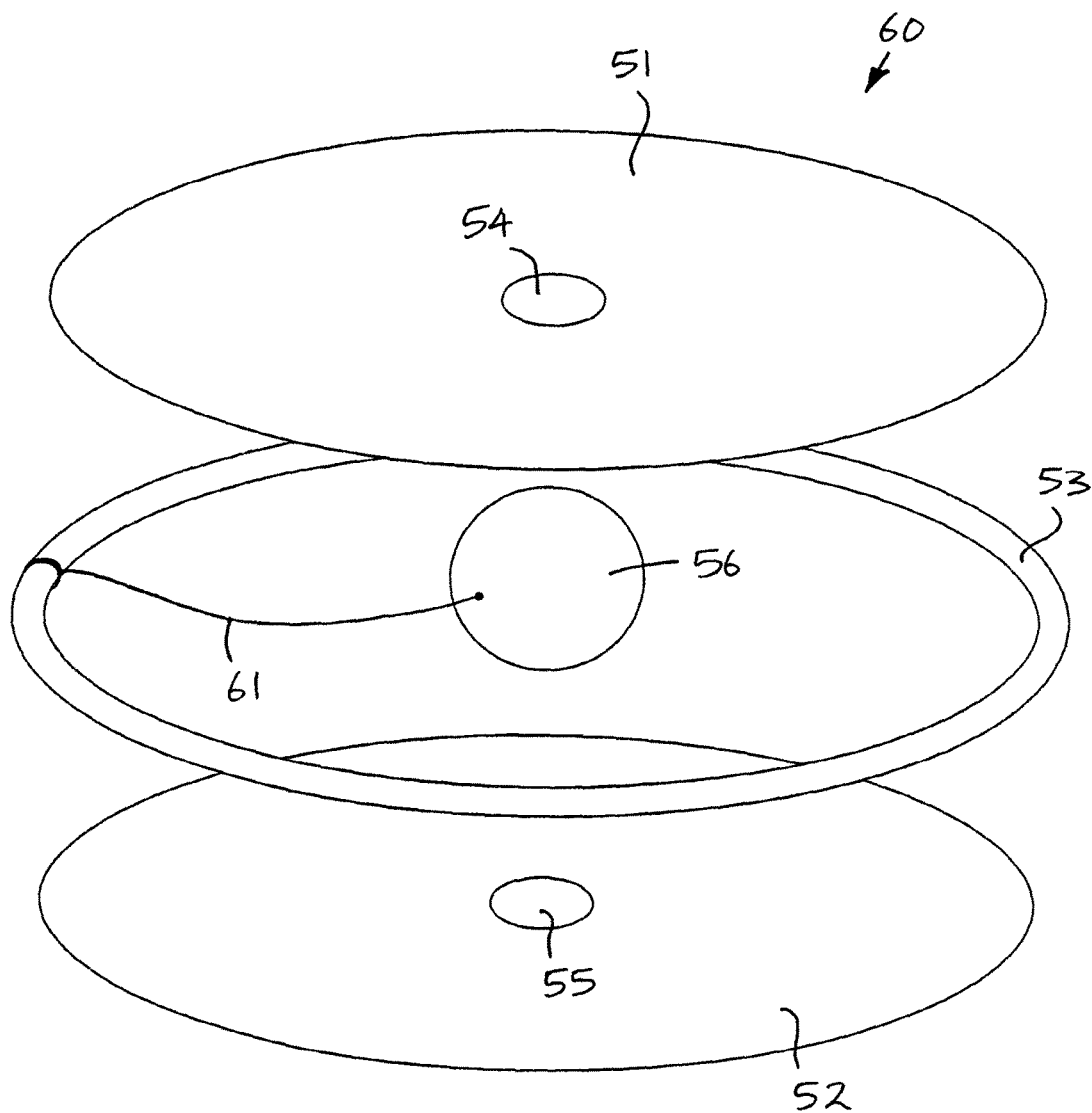
FIGS. 21 and 22 are exploded, perspective views of other seals according to the invention.

The ball 56 may be tethered to the O-ring 53 by means of a tether line 61, as illustrated in the distal seal 60 of FIG. 21. The tether line 61 thus prevents inadvertent passage of the ball 61 out from between the sealing members 51, 52 through one of the accessways 54, 55.

Figure 22:
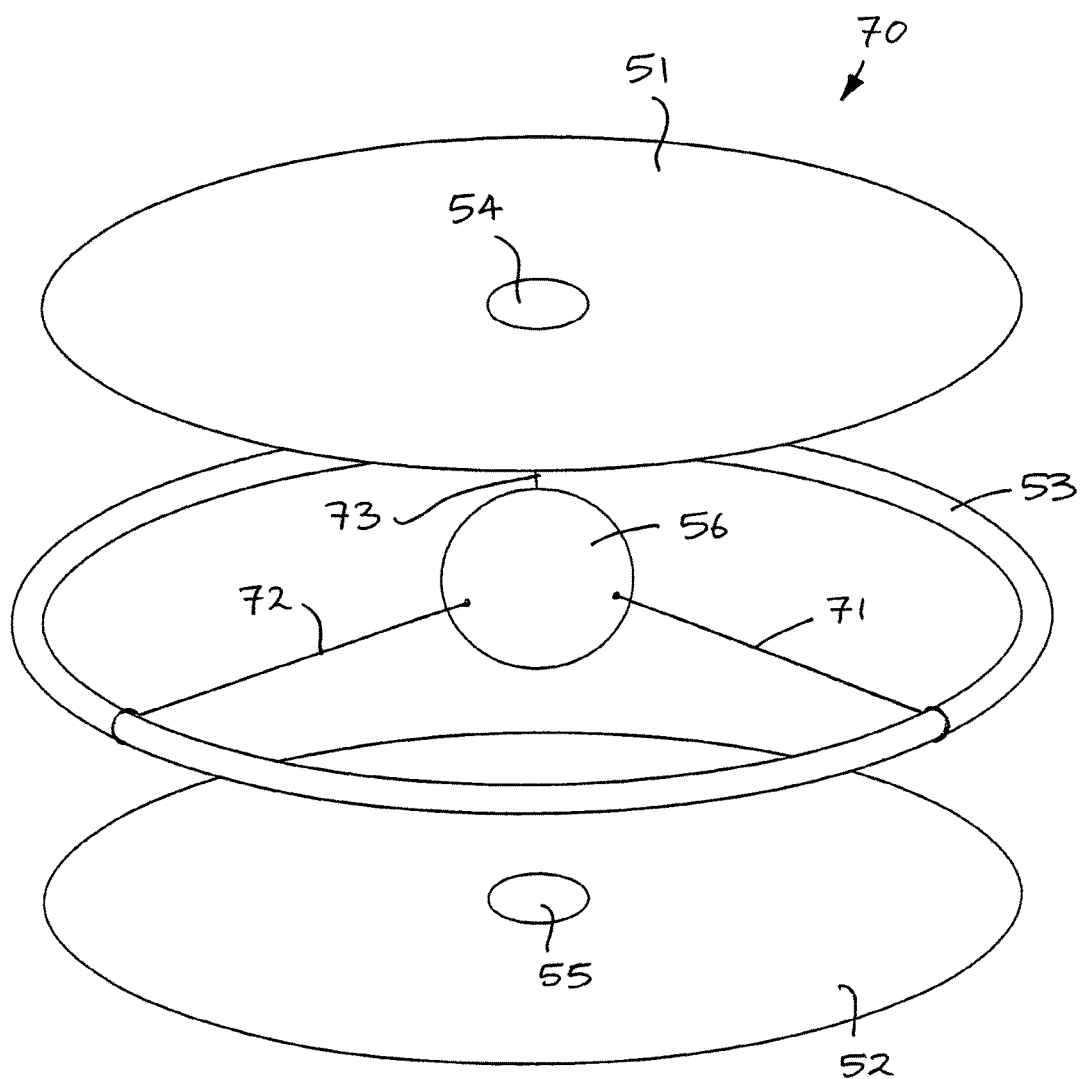

In the distal seal 70 of FIG. 22, the ball 56 is connected to the O-ring 53 by three resilient members 71, 72, 73, for example elastic bands. The resilient members 71, 72, 73 act to bias the ball 56 towards the central sealing position occluding the two accessways 54, 55. In this manner, upon removal of the surgeon's atm 4 from the distal seal 70, the ball 56 is moved back to the sealing position to prevent loss of insufflation gas from the body cavity.

Figure 24:
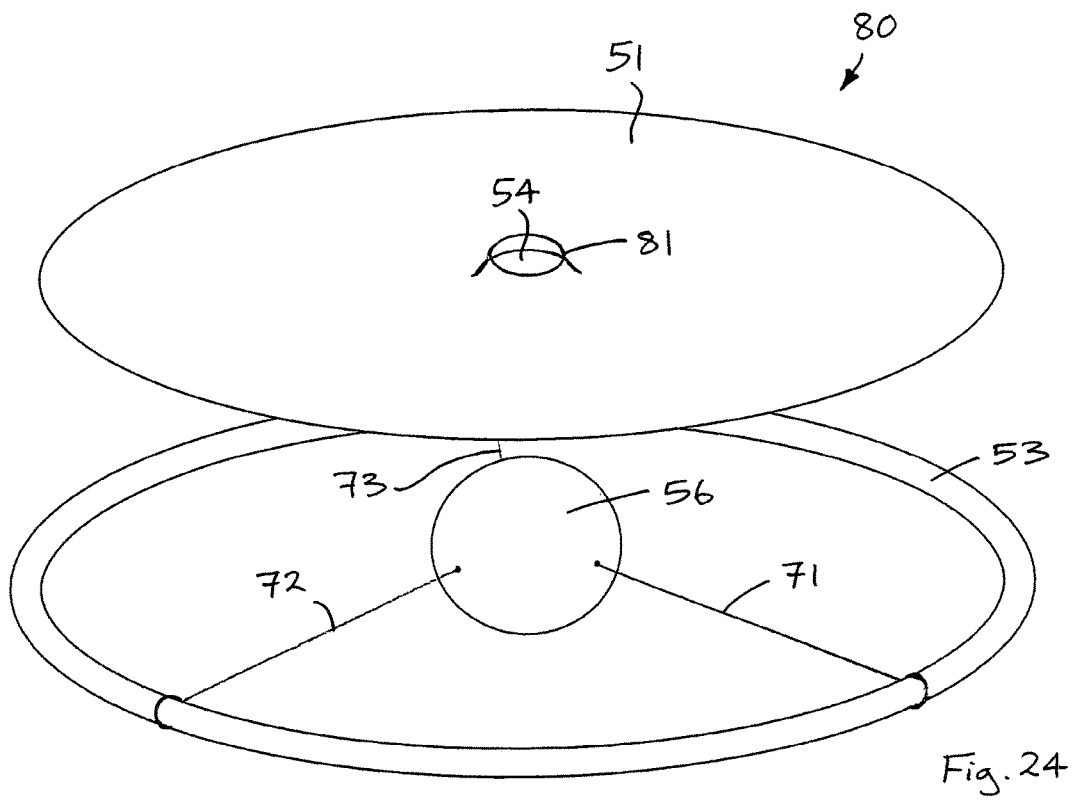
FIG. 24 is an exploded, perspective view of the seal of FIG. 23.
Figure 23:
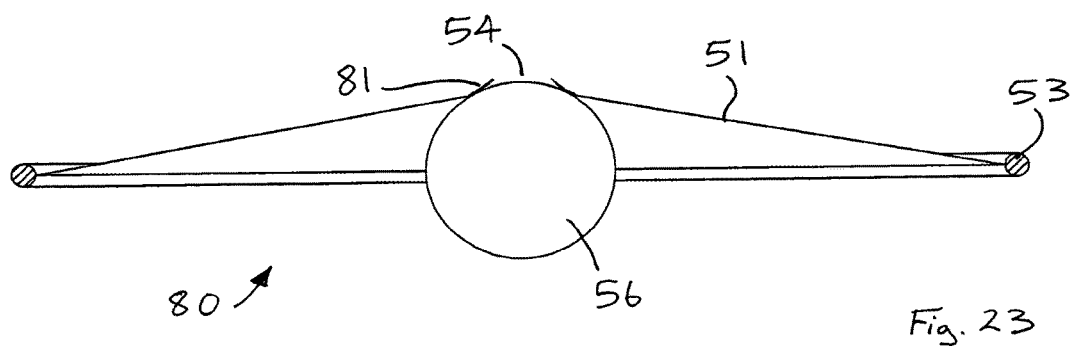
FIG. 23 is a cross-sectional, front view of a further seal according to the invention.

A collar 81 may be provided around the accessway 81 on the proximal surface of the proximal sealing member 51, as illustrated in FIGS. 23 and 24. It has been found that such a collar arrangement enhances the sealing of the ball 56 to the sealing member 51 around the opening 54.

Figure 25:
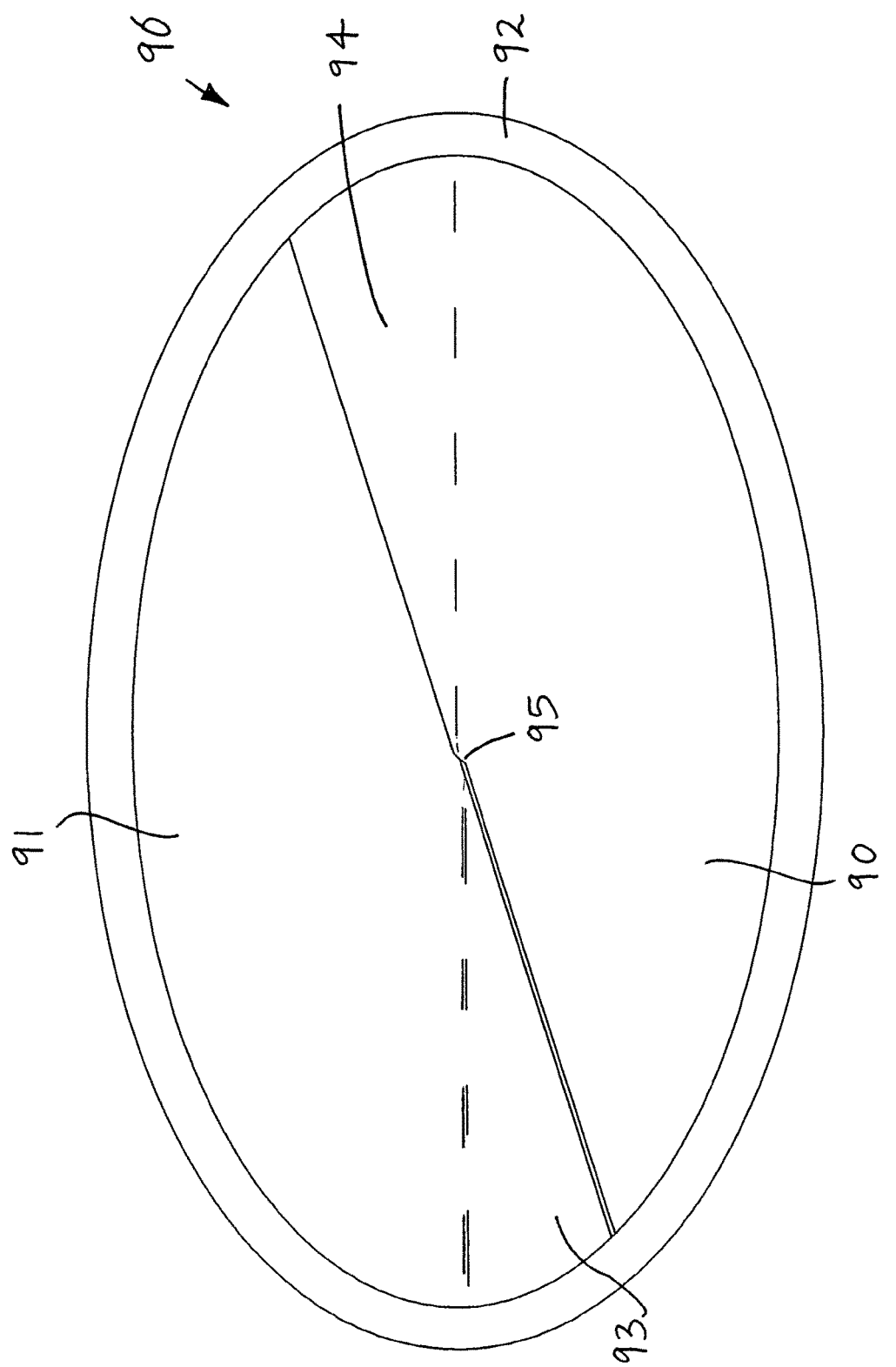
FIG. 25 is a perspective view of another seal according to the invention.
Figure 26:
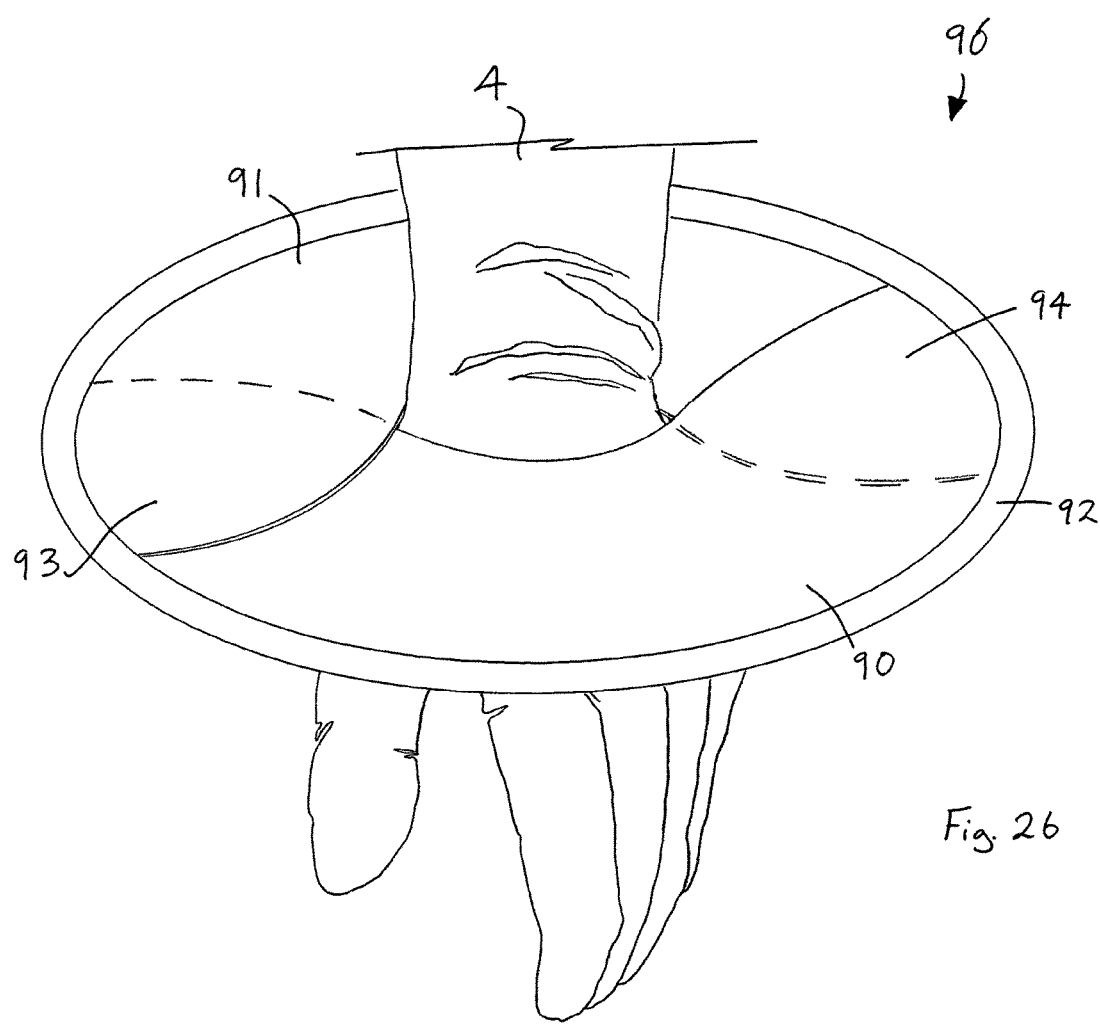
FIG. 26 is a perspective view of the seal of FIG. 25, in use.

In FIGS. 25 and 26 there is illustrated another distal seal 96 according to the invention, which is suitable for use with the surgical device 1.

The distal seal 96 comprises two sealing members 90, 91. In this case each sealing member 90, 91 is provided in the form of a sheet coupled to a circumferentially extending O-ring 92.

The sealing members 90, 91 overlap one another such that a portion of the sealing member 90 overlaps a portion of the sealing member 91 along a first overlap region 94, and a portion of the sealing member 91 overlaps a portion of the sealing member 90 along a second overlap region 93, as illustrated in FIG. 26. In this manner the distal seal 96 is normally closed to prevent escape of insufflation gas between the sealing members 90, 91 (FIG. 25).

The sealing members 90, 91 are manipulable to facilitate sealed passage of an object, such as the surgeon's arm 4, through the distal seal 96 at the junction 95 of the two overlap regions 93, 94 to gain access to an internal body cavity and/or internal body organs, as illustrated in FIG. 26.

A suitable material for the sealing members 90, 91 to enable manipulation of the sealing members 90, 91 is a flexible material, such as silicone or latex. The sealing members 90, 91 are preferably also of a resilient material to ensure that the sealing members 90, 91 return to the normally closed position after withdrawal of the surgeon's arm 4.

In this case the area of the two overlap regions 93, 94 is substantially equal.

Figure 27:
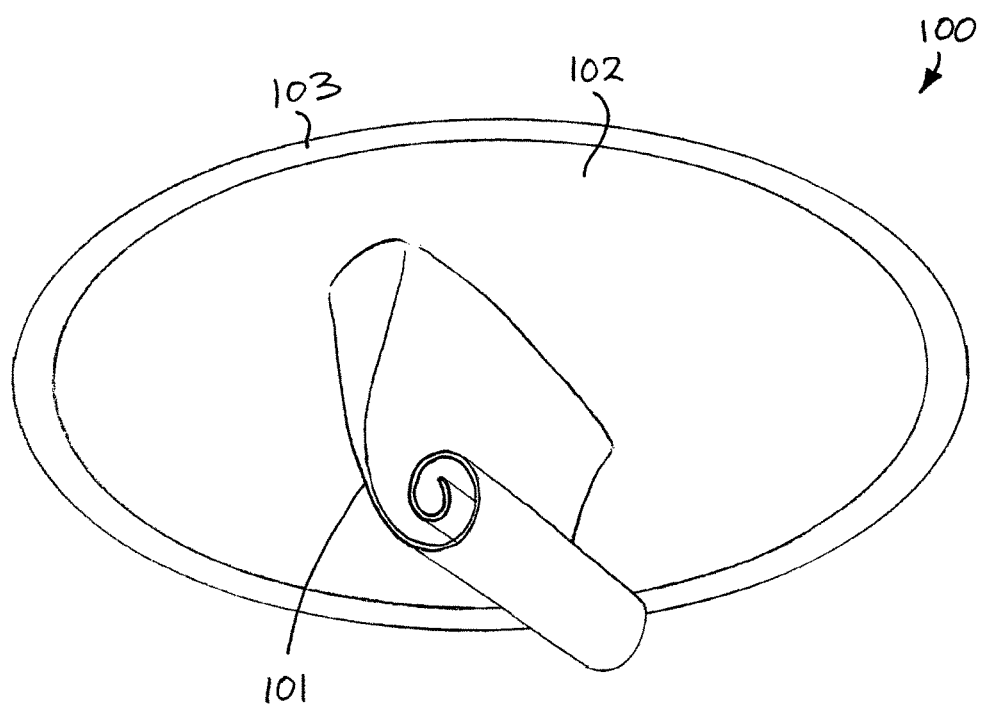
FIGS. 27 and 28 are views similar to FIGS. 25 and 26 of another seal according to the invention.
Figure 28:
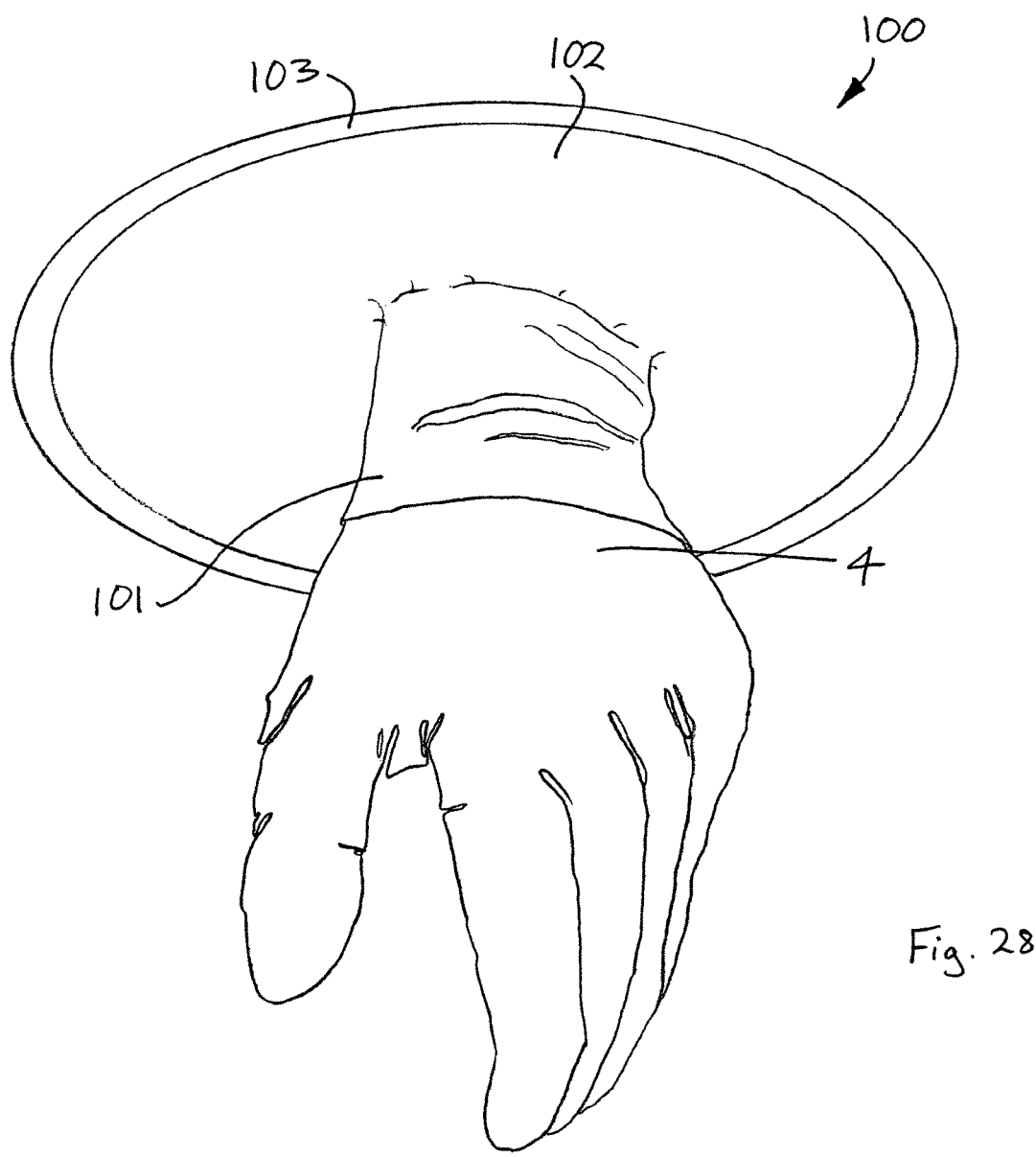

Referring next to FIGS. 27 and 28, there is illustrated another distal seal 100 according to the invention, which is suitable for use with the surgical device 1.

The seal 100 comprises a sleeve 101 through which an object, such as a surgeon's arm 4, may be passed and an annular platform 102. The platform 102 has an O-ring 103 to stiffen the platform 102.

The sleeve 101 is configured to curl-up upon itself as illustrated in FIG. 27, and thereby bias itself into a normally closed configuration. In this closed configuration the curled sleeve 101 prevents the escape of insufflation gas from a body cavity through the distal seal 100.

To gain access to an internal body cavity or internal body organs, the surgeon inserts his arm 4 through the sleeve 101 which causes the sleeve 101 to uncurl (FIG. 28).

It will be appreciated that other self-closing configurations are possible for the sleeve 101. For example, the sleeve 101 may alternatively be configured to twist-up upon itself to the closed configuration.

Figure 29:
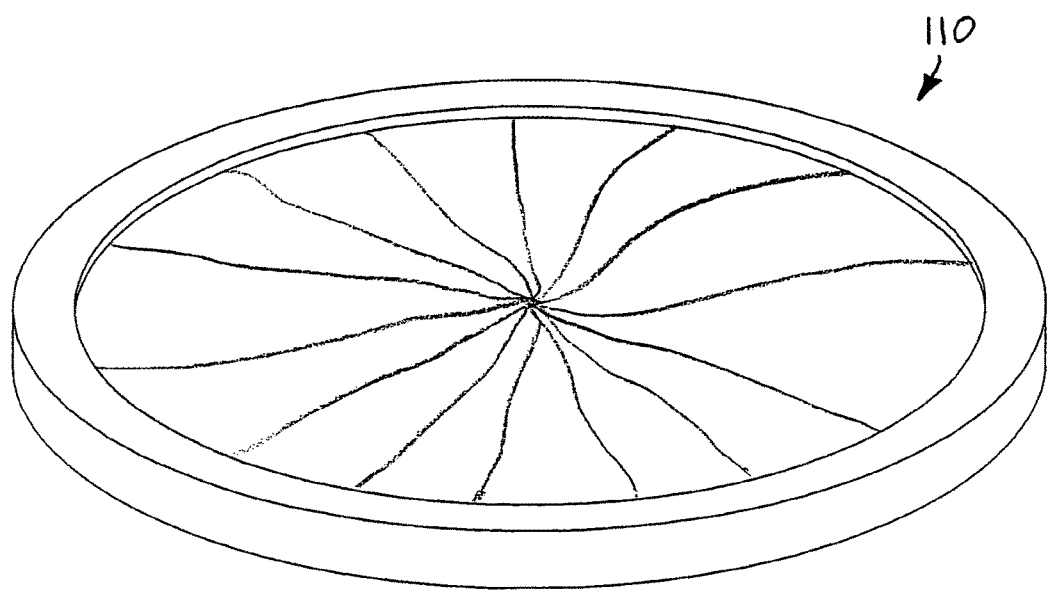
FIG. 29 is a perspective view of another seal of the device of FIG. 1.
Figure 30:
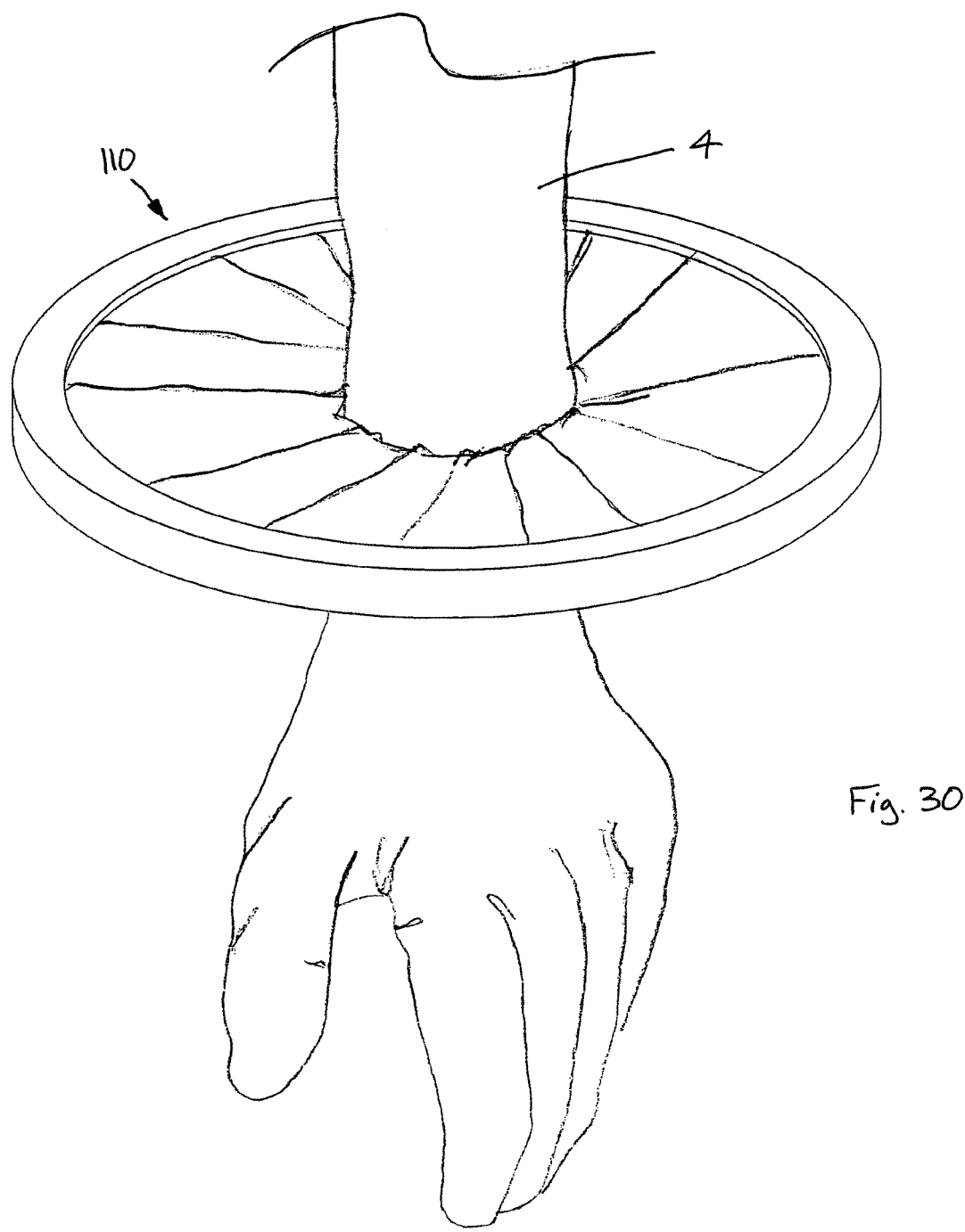
FIGS. 30 and 31 are perspective views of the seal of FIG. 29, in use.

It will be understood that a wide variety of possible configurations for the proximal seal of the surgical device 1 are possible within the scope of this invention. For example, the proximal seal may comprise an iris valve 110, as illustrated in FIGS. 29 and 30.

The proximal seal may additionally or alternatively be in the form of one of the seals described previously with reference to FIGS. 2 to 28.

Figure 31:
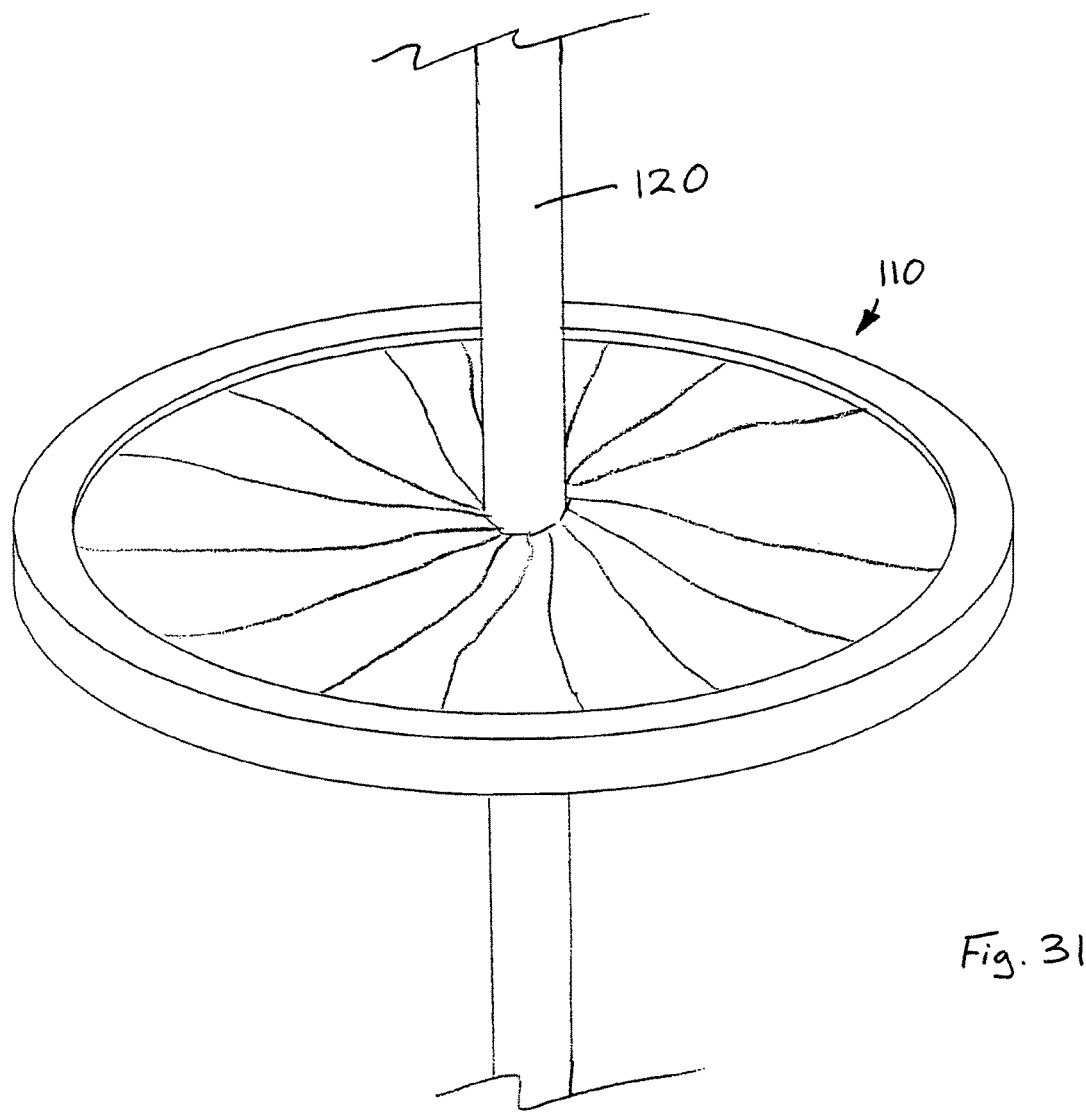
Figure 32:
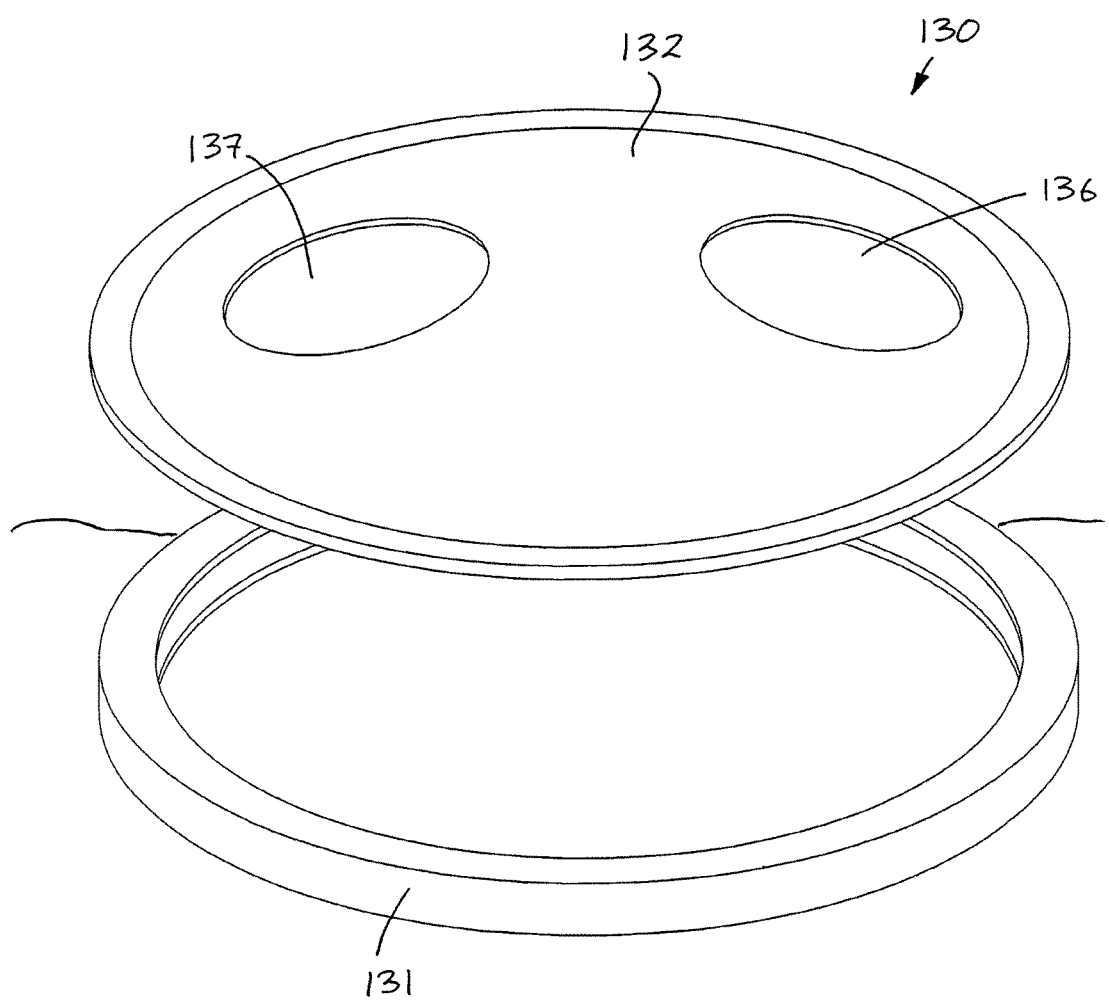
FIG. 32 is an exploded, perspective view of another surgical device according to the invention.
Figure 33:
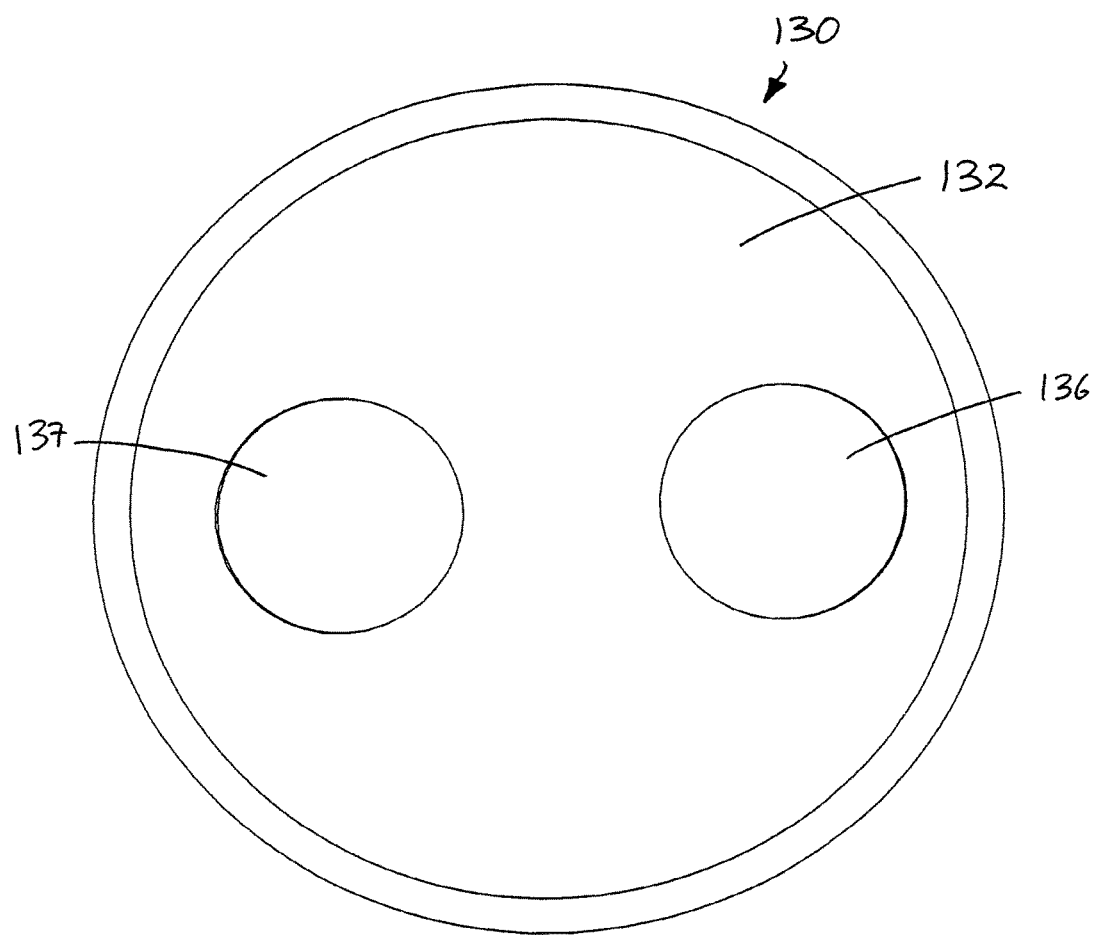
FIG. 33 is a plan view of the device of FIG. 32.
Figure 34:
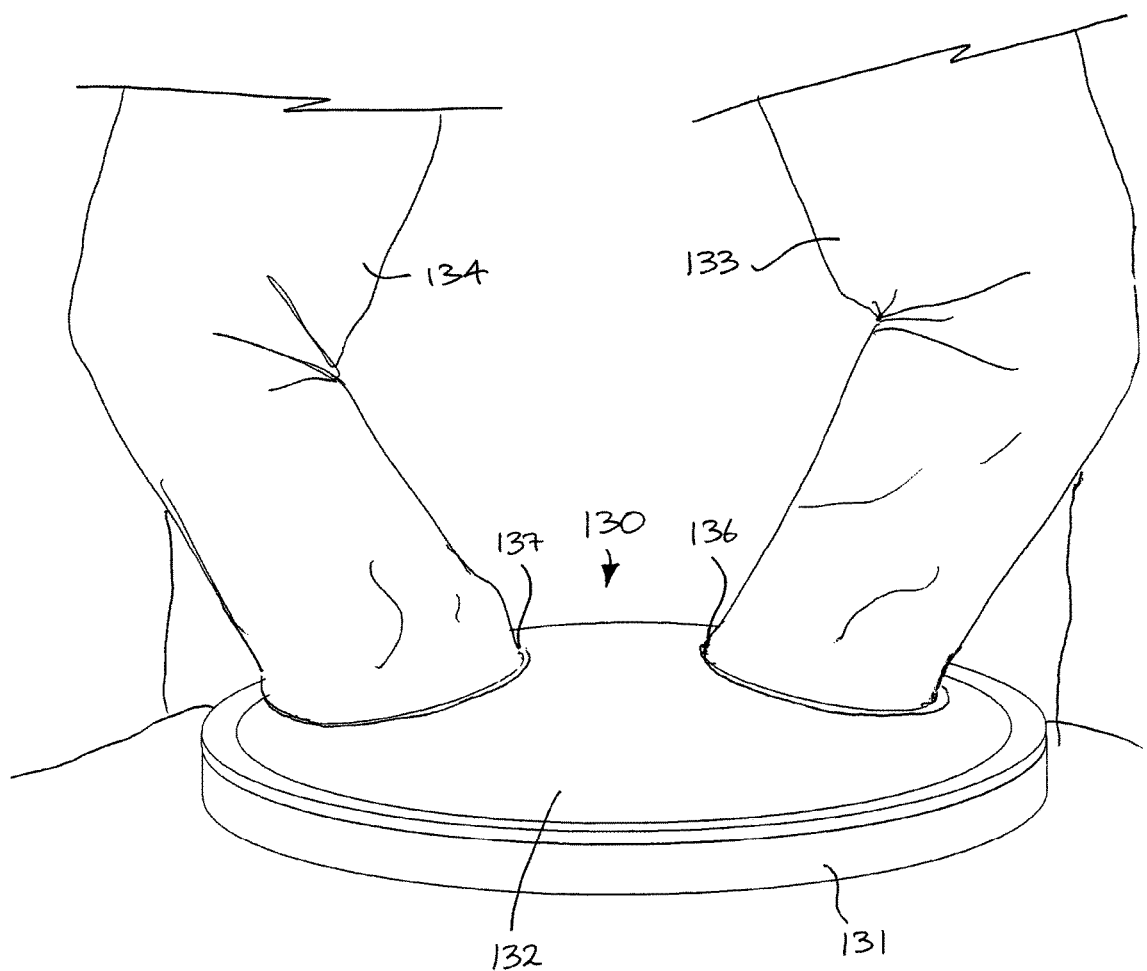
FIG. 34 is a perspective view of the device of FIG. 32, in use.

Furthermore it will be appreciated that the surgical device 1 and the seals according to the invention are suitable for sealing a variety of objects, such as a surgical instrument 120, as illustrated in FIG. 31.

The surgical device 1 of the invention could be used in configuration with a wound retractor. In one case the device 1 could be releasably mounted to the retractor. In another case the device 1 could be provided integral with the retractor.

Referring now to FIGS. 32 to 37 there is illustrated another surgical device 130 according to the invention.

The device 130 comprises a wound retractor 131 and a domed sealing member 132.

The wound retractor 131 is similar to the surgical wound retractor described in international patent application number PCT/IE00/00126, the relevant contents of which are incorporated herein by reference. In particular, the retractor 131 comprises a distal O-ring 139 for insertion into a wound opening 138, a retracting sleeve 135, and a proximal annular ring means.

Figure 35:
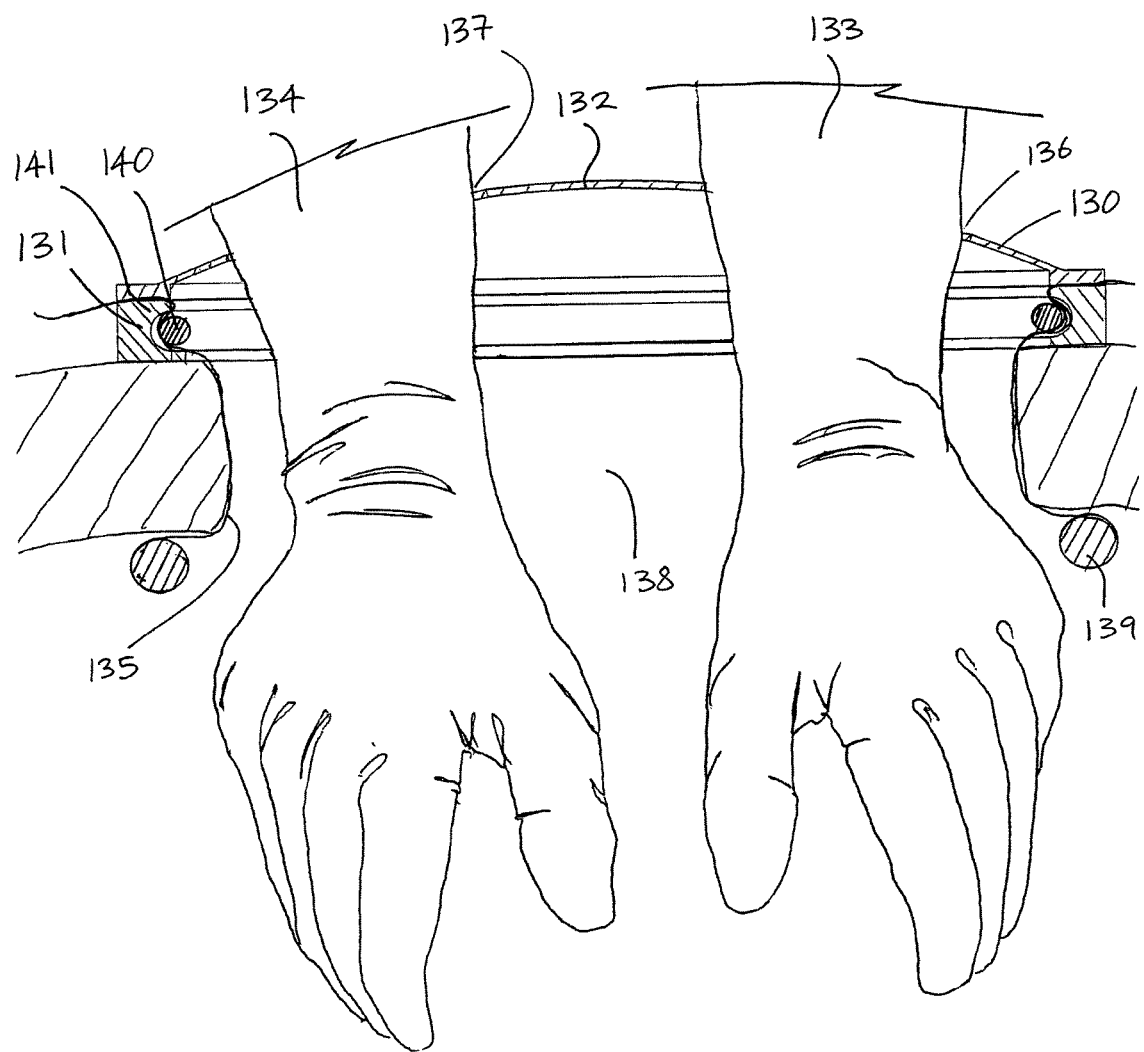
FIG. 35 is a partially cross-sectional, front view of the device of FIG. 32, in use.

The proximal annular ring means comprises an outer ring 141 and an inner O-ring 140 which is partially located in a recess of the outer ring 141. The sleeve 135 passes through the proximal annular ring means between the inner and outer rings 140, 141 (FIG. 35).

To retract the wound opening 138, the distal O-ring 139 is inserted into the wound opening 138 to another the wound retractor 131 in position in the wound opening 138. The proximal rings 140, 141 are then moved downwardly while pulling the sleeve 135 upwardly to move the sleeve 135 lining the wound laterally to a retracting configuration, and thereby retract the sides of the wound opening 138 laterally.

The sealing member 132 comprises two accessways 136, 137 through the sealing member 132, through which the left and right arms 133, 134 of a surgeon may be extended to gain access to an internal body cavity or internal body organs.

By providing two access openings 136, 137 in the sealing member 132, this enables the surgeon to extend both arms 133, 134 through the retracted wound opening 138 in a sealed manner. Thus it is possible for the surgeon to perform procedures with both hands, such as suturing, while maintaining the pneumoperitoneum.

Figure 36:
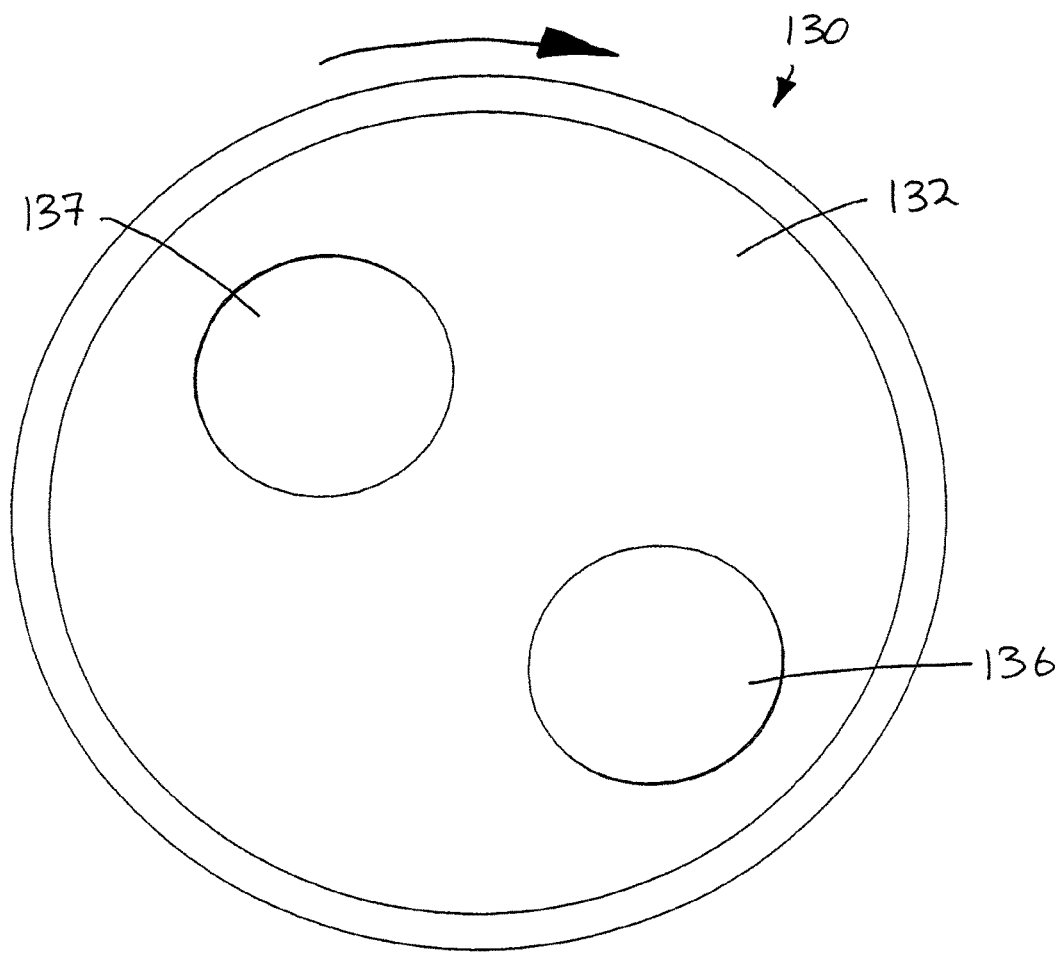
FIGS. 36 and 37 are plan views of the device of FIG. 32, in use.
Figure 37:
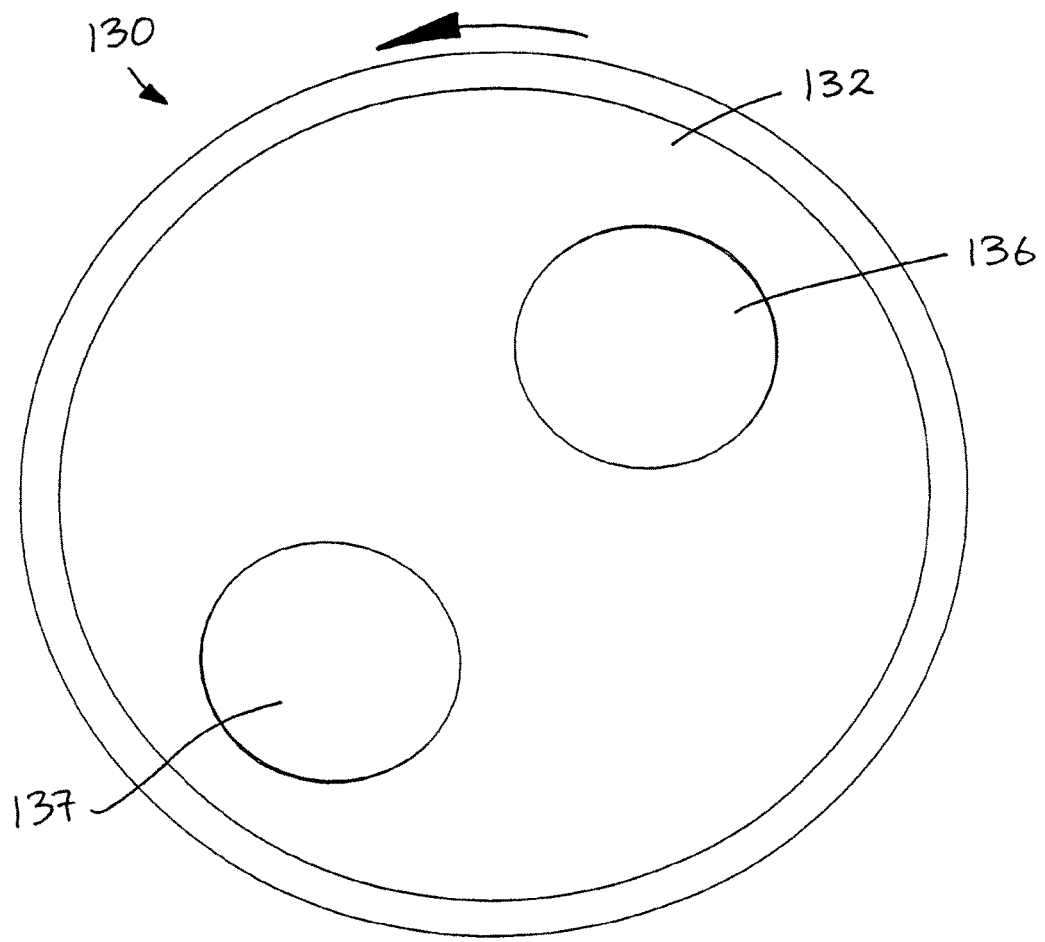

The sealing member 132 is releasably mounted to the wound retractor 131 in a retractable manner. Thus as illustrated in FIGS. 36 and 37, it is relatively simple to rotate the sealing member 132 and thus the accessways 136, 137 to enable the surgeon access a desired region or organ within the sealed internal body cavity.

It will be appreciated that means may be provided to seal the accessways 136, 137 when not in use, and to seal around an object, such as the surgeon's arms 133, 134, extending through the accessways 136, 137.

Figure 38:
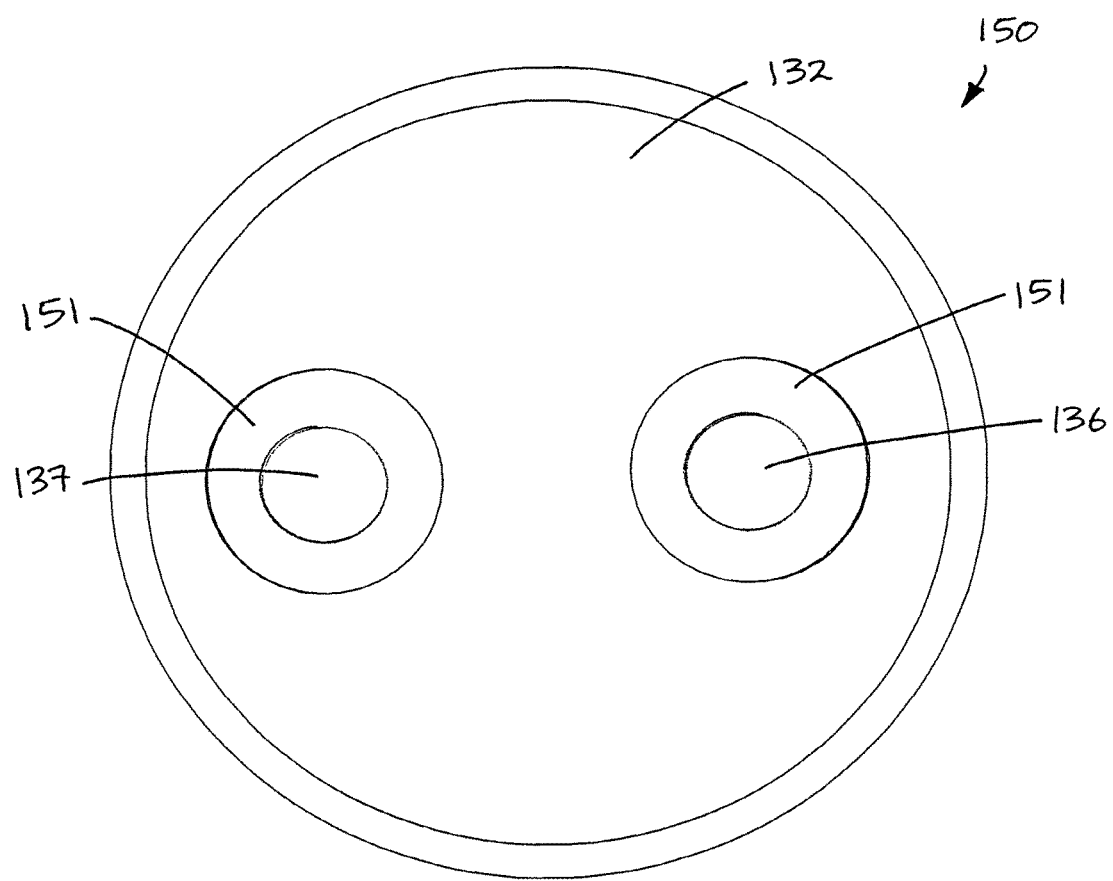
FIGS. 38 to 40 are plan views of other surgical devices according to the invention.

In the surgical device 150 of FIG. 38, lip seals 151 are provided at each accessway 136, 137 to effect the sealing function.

Figure 39:
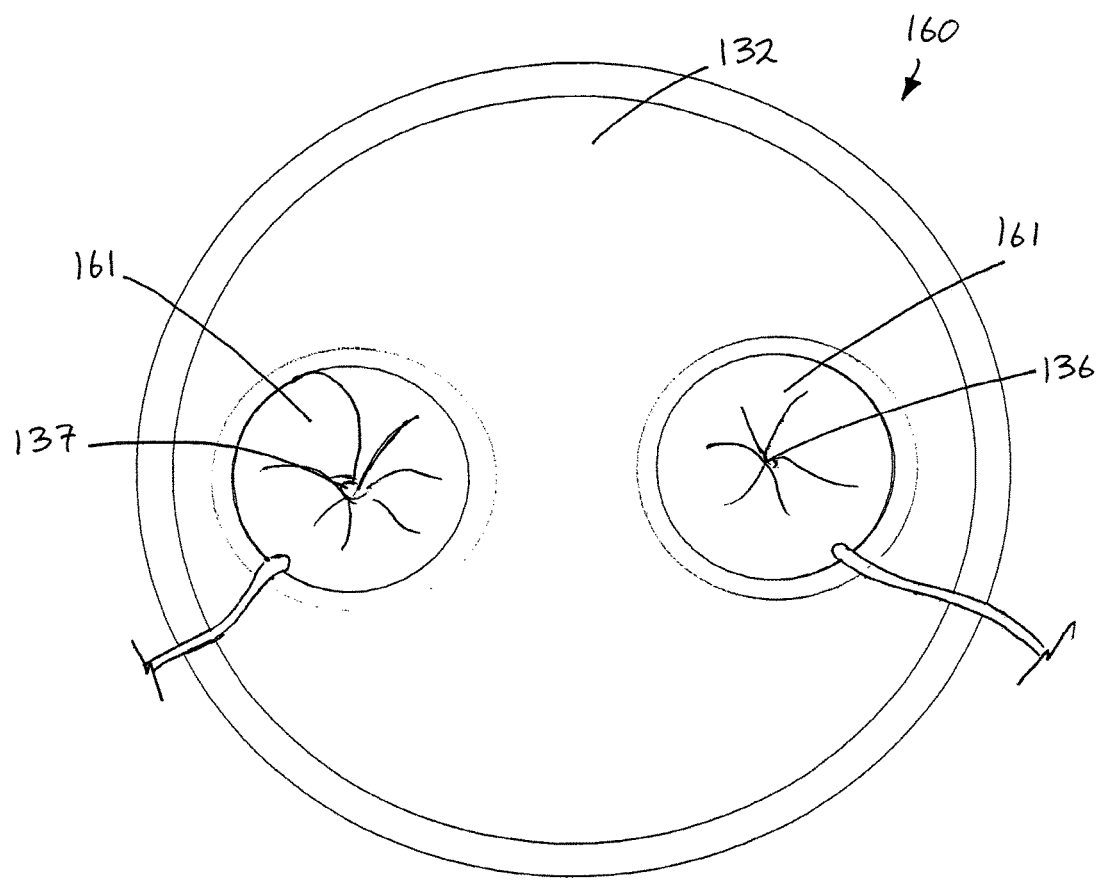

In the surgical device 160 of FIG. 39, each accessway 136, 137 has an inflatable chamber 161. By passing a pressurised fluid into the chamber 161 the accessways 136, 137 may be sealed. In this case the chamber 161 is defined by a sleeve turned back on itself to define an outer sleeve section and an inner sleeve section with the chamber defined therebetween. The inner sleeve section is twisted and the outer sleeve section is substantially cylindrical. Upon passage of an object, such as the surgeon's arms 133, 134 through the inflated sleeve, the sleeve everts. In this regard the chamber 161 is similar to the medical device described in International patent application number PCT/IE99/00123, the relevant contents of which are incorporated herein by reference.

Figure 40:
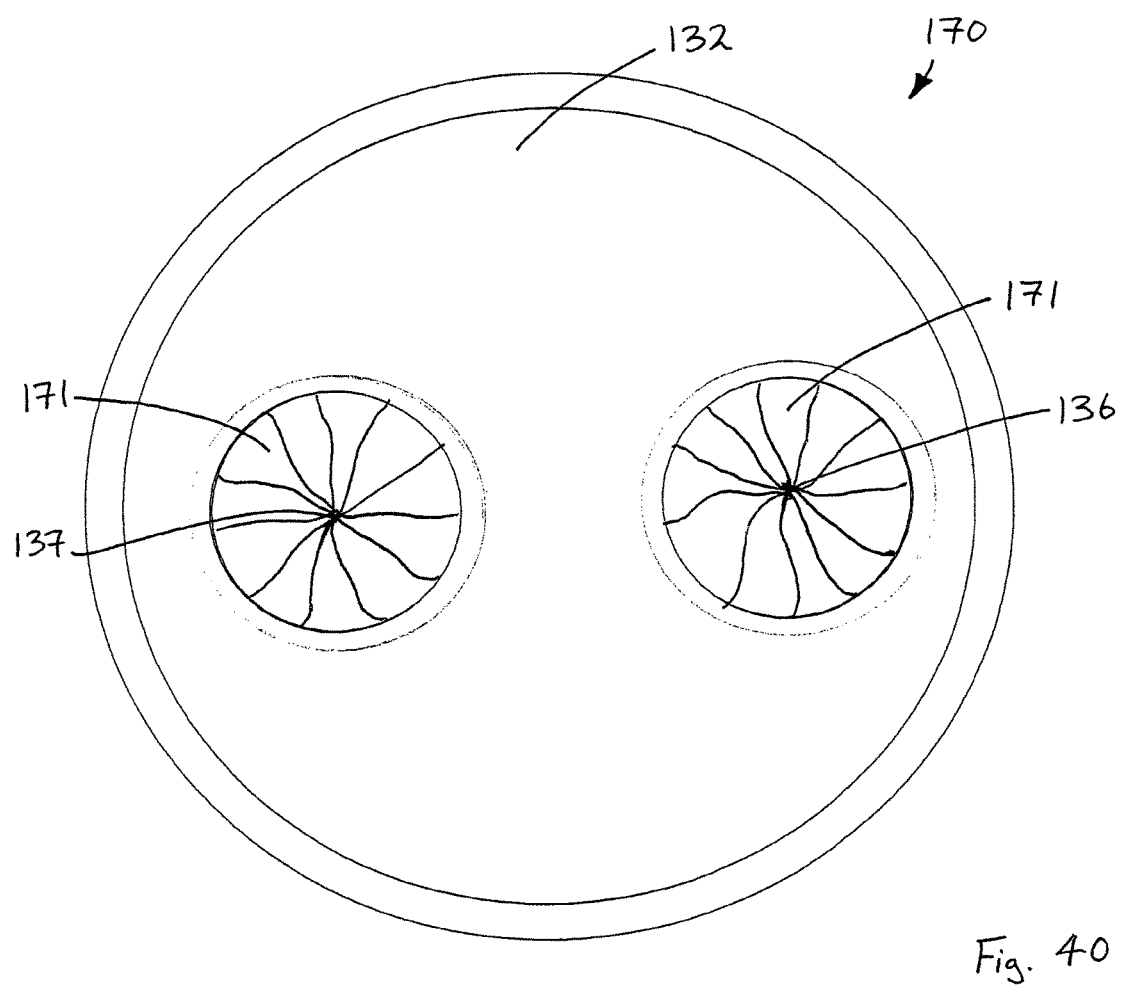

In the surgical device 170 of FIG. 40, iris valves 171 are provided at each accessway 136, 137 to effect the sealing function.

Figure 41:
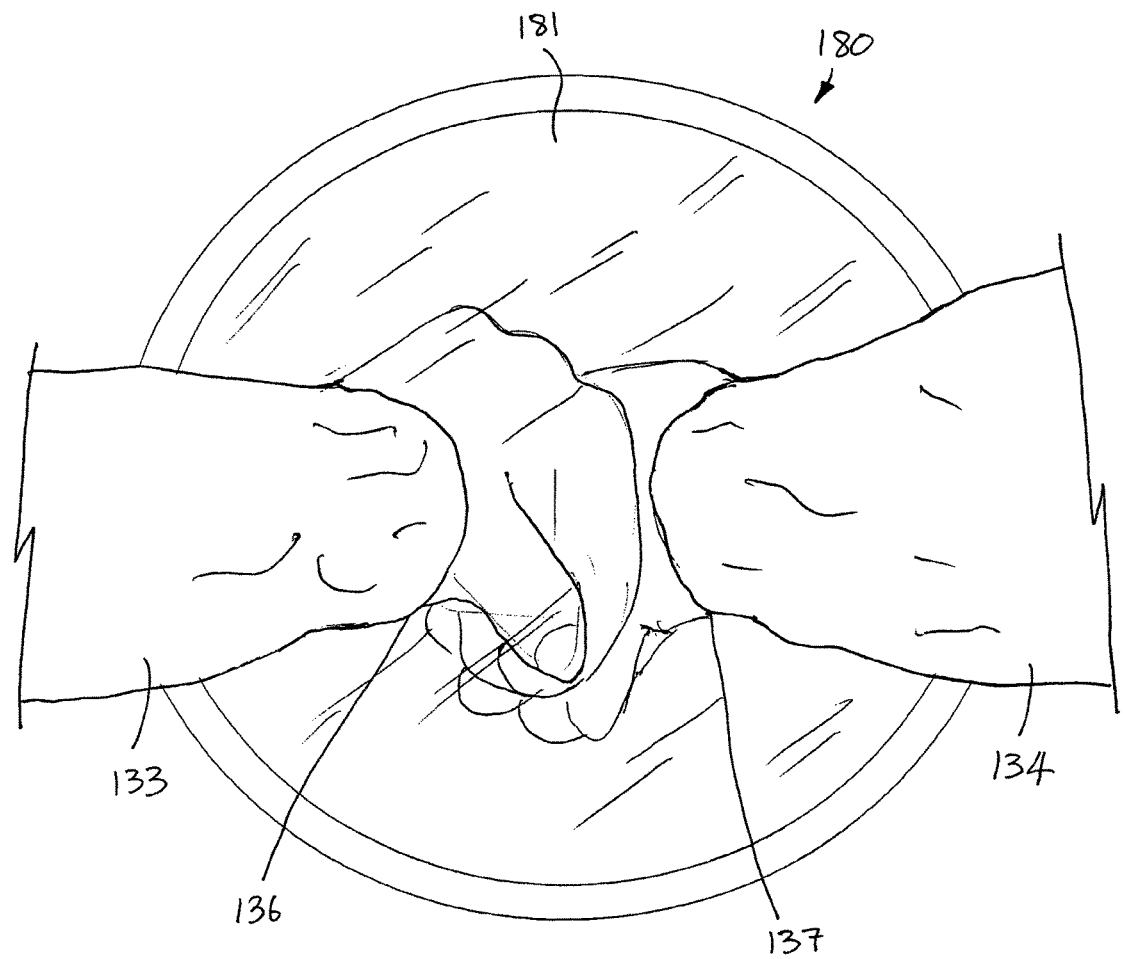
FIG. 41 is a plan view of a further surgical device according to the invention, in use.

As illustrated in the surgical device 180 of FIG. 41, the sealing member 181 may be at least partially transparent for enhanced visualisation of the sealed internal body cavity and/or internal body organs.

It will be appreciated that the surgical devices according to the invention may also be configured to seal objects other than a human arm extended through an accessway of the sealing member 132, for example a surgical instrument.

Figure 42:
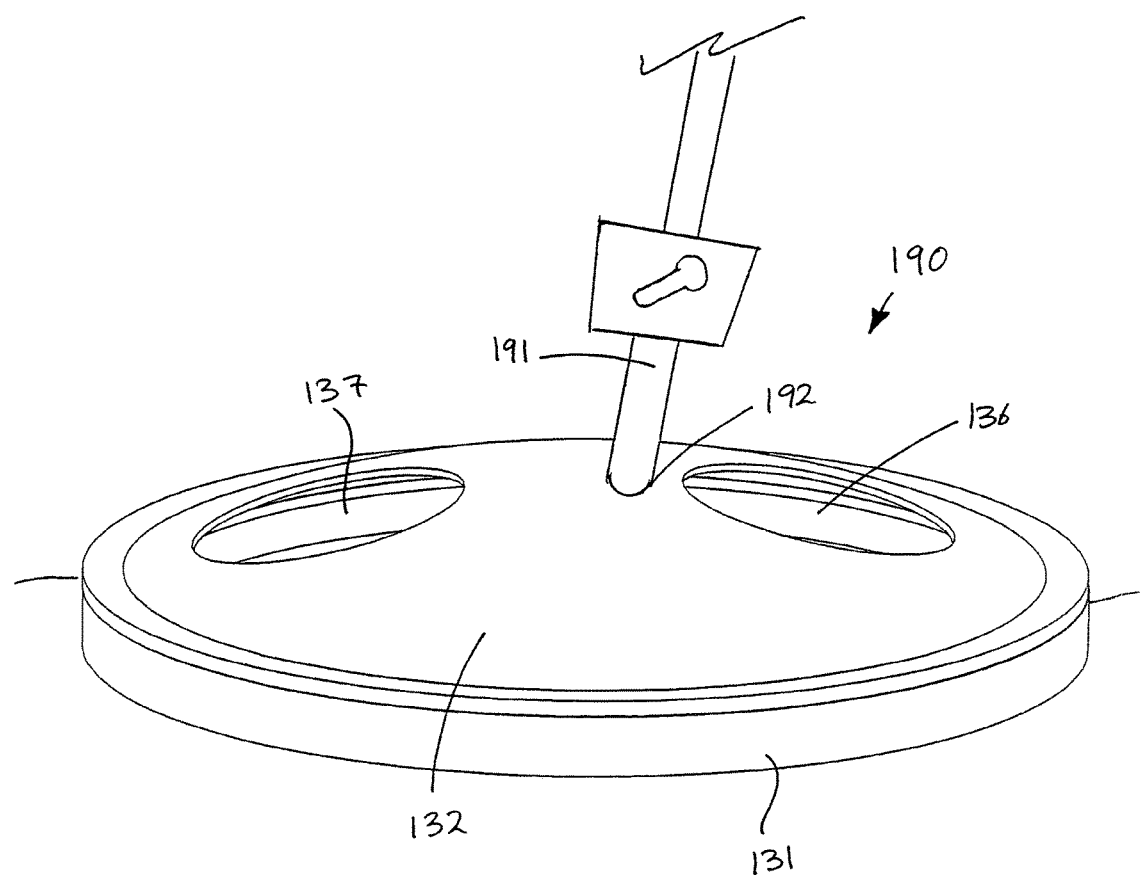
FIGS. 42 and 43 are perspective views of other surgical devices according to the invention.

Furthermore an accessway 192 may be provided through the sealing member 132 for a surgical instrument 191 in addition to the two arm accessways 136, 137, as illustrated in the surgical device 190 of FIG. 42.

Figure 43:
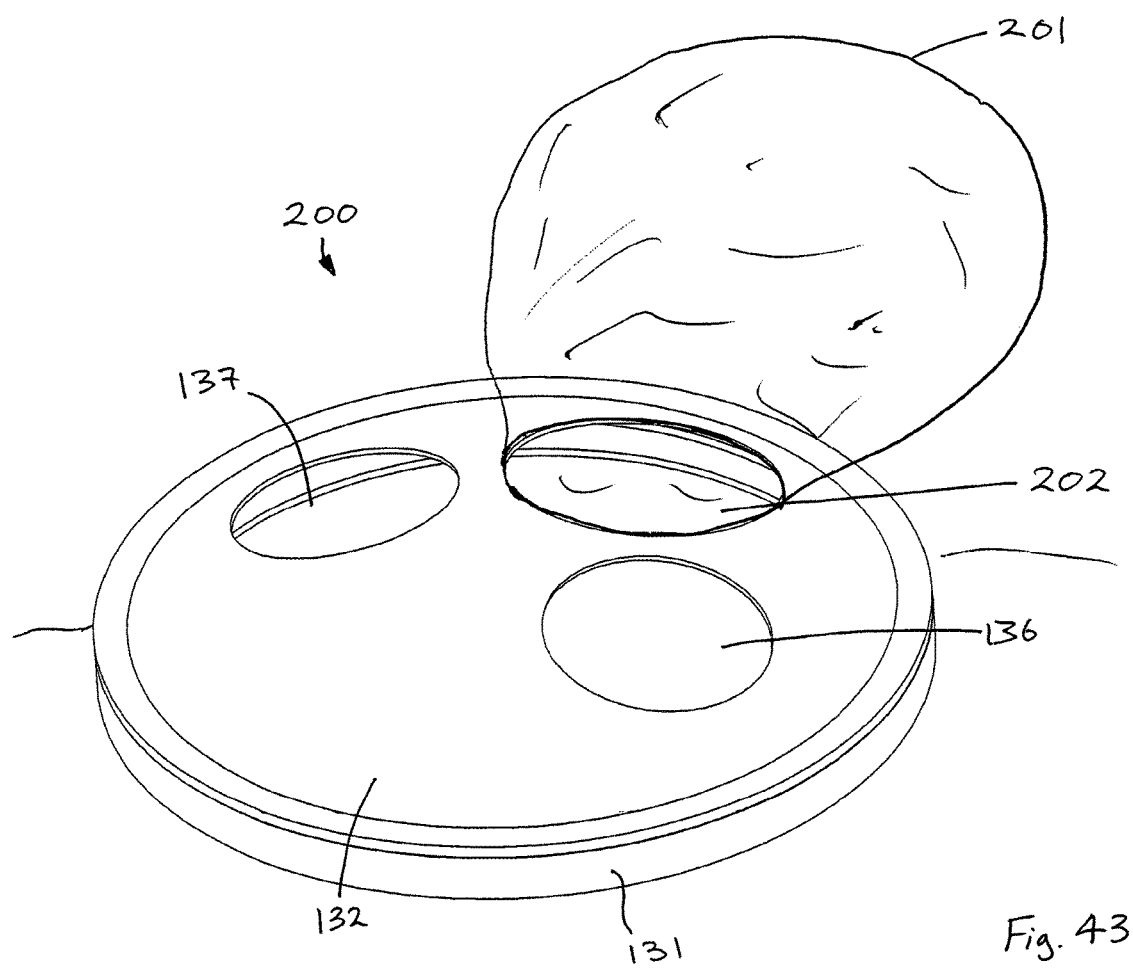
Figure 44:
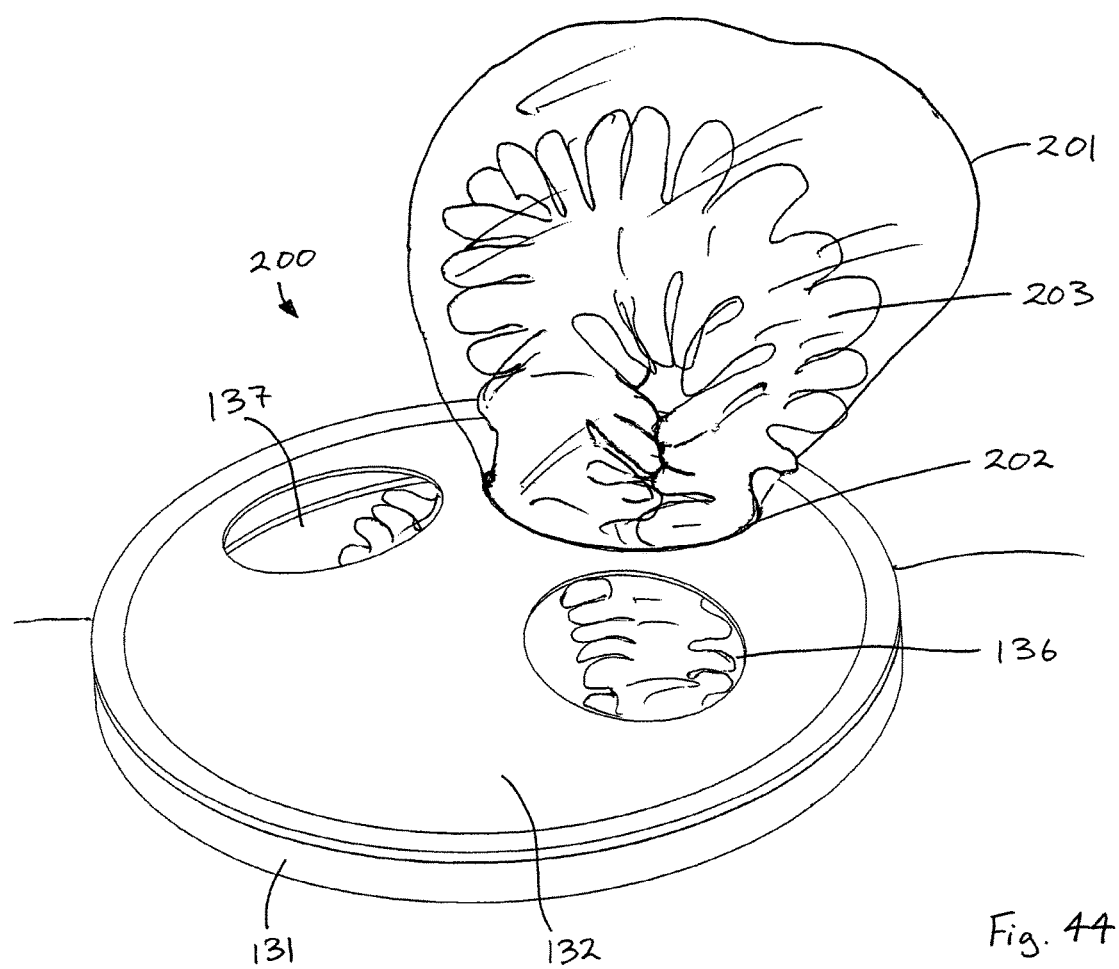
FIG. 44 is a perspective view of the device of FIG. 43, in use.

As a further alternative a bag 201 may be attached to the sealing member 132 at a bag opening 202, as illustrated in the surgical device 200 of FIGS. 43 and 44. The bag 201 is gas-tightly sealed to the sealing member 132 at the opening 202 to maintain the pneumoperitoneum. An internal organ of the patient, such as portion of the colon 203, may be temporarily moved into the bag 201 for closer examination and/or to create extra space within the body cavity.

The invention is not limited to the embodiments hereinbefore described, with reference to the accompanying drawings, which may be varied in construction and detail.

The invention claimed is:

1. A surgical method for providing access through a wound opening, the method including:
   inserting a wound protector into the wound opening, wherein inserting the wound protector includes:
      positioning a distal ring of the wound protector such that the distal ring is distal of the wound opening,
      positioning a proximal ring assembly of the wound protector such that the proximal ring assembly is proximal of the wound opening, the proximal ring assembly having a proximal ring member and a sealing member, the sealing member having a plurality of access portions that provide access through the sealing member, and
      positioning a sleeve of the wound protector in the wound opening, the sleeve extending between the proximal ring member and the distal ring; and
   rotatably moving at least one of the plurality of access portions about a central longitudinal axis of the proximal ring assembly from a first rotational position relative to the proximal ring member to a second rotational position relative to the proximal ring member, wherein the first rotational position is different than the second rotational position.

2. The surgical method of claim 1, wherein rotatably moving at least one of the plurality of access portions about the central longitudinal axis of the proximal ring assembly includes rotatably moving the at least at least one of the plurality of access portions along a circular path, a central longitudinal axis of the at least one of the plurality of access portions being offset from the central longitudinal axis of the proximal ring assembly.

3. The surgical method of claim 1, wherein rotatably moving at least one of the plurality of access portions about the central longitudinal axis of the proximal ring assembly includes rotatably moving a first access portion and a second access portion about the central longitudinal axis of the proximal ring assembly, wherein the first access portion is on a first side of the central longitudinal axis of the proximal ring assembly, and the second access portion is on a second side of the central longitudinal axis of the proximal ring assembly, wherein the first and second sides are opposite sides of the central longitudinal axis of the proximal ring assembly.

4. The surgical method of claim 1, wherein rotatably moving at least one of the plurality of access portions about the central longitudinal axis of the proximal ring assembly includes rotatably moving at least three access portions about the central longitudinal axis of the proximal ring assembly.

5. The surgical method of claim 4, wherein a path traveled by one of the at least three access portions is shorter than paths traveled by the other of the at least three access portions.

6. The surgical method of claim 1, further including:
inserting a first object through a first access portion of the plurality of access portions; and
inserting a second object through a second access portion of the plurality of access portions, the first and second objects having different width dimensions, and the first and second access portions having different width dimensions.

7. The surgical method of claim 1, further including inserting an object through the at least one of the plurality of access portions, the at least one of the plurality of access portions including a sealing element that provides a seal around an exterior surface of the object, wherein the seal is maintained during rotational movement of the at least one of the plurality of access portions.

8. A surgical method for providing access through a wound opening, the method including:
inserting a wound protector into the wound opening, wherein inserting the wound protector includes:
positioning a distal ring of the wound protector such that the distal ring is distal of the wound opening,
positioning a proximal ring assembly of the wound protector such that the proximal ring assembly is proximal of the wound opening, the proximal ring assembly having a proximal ring member and a sealing member, the sealing member having a plurality of access portions that provide access through the sealing member, and
positioning a sleeve of the wound protector in the wound opening, the sleeve extending between the proximal ring member and the distal ring; and
rotating the sealing member about a central longitudinal axis of the proximal ring assembly in at least one of a clockwise and a counterclockwise direction.

9. The surgical method of claim 8, further including inserting at least one object through the at least one access portion.

10. The surgical method of claim 9, wherein the sealing member is rotated with the object within the at least one access portion.

11. The surgical method of claim 9, further including sealing around an exterior surface of the object with at least one seal member in the at least one access portion.

12. The surgical method of claim 11, wherein the sealing takes place in an area proximal to the proximal ring member.

13. The surgical method of claim 8, wherein the at least one access portion includes first, second, and third access portions, wherein each of the first, second, and third access portions includes a central longitudinal axis, and wherein the central longitudinal axes of the first, second, and third access portions define vertices of a triangle.

14. A surgical method for providing access through a wound opening, the method including:
inserting a wound protector into the wound opening, wherein inserting the wound protector includes:
positioning a distal ring of the wound protector such that the distal ring is distal of the wound opening,
positioning a proximal ring assembly of the wound protector such that the proximal ring assembly is proximal of the wound opening, the proximal ring assembly having a proximal ring member and a sealing member, the sealing member having a plurality of access portions that provide access through the sealing member, and
positioning a sleeve of the wound protector in the wound opening, the sleeve extending between the proximal ring member and the distal ring; and
inserting a first object through a first access portion of the sealing member;
inserting a second object through a second access portion of the sealing member; and
repositioning the first object and the second object, wherein repositioning includes rotating the sealing member about a central longitudinal axis of the proximal ring assembly.

15. The surgical method of claim 14, further including sealing around an external surface of the first object with a first sealing member of the first access portion.

16. The surgical method of claim 15, wherein the sealing is maintained during repositioning.

17. The surgical method of claim 14, further including inserting a third object through a third access portion of the sealing member.

18. The surgical method of claim 17, wherein inserting the first, second, and third objects in the first, second, and third access portions positions the first, second, and third objects in a triangular configuration on the sealing member.

19. The surgical method of claim 14, wherein inserting the first object through the first access portion includes introducing the first object into the first access portion at an area proximal to the proximal ring member.

20. The surgical method of claim 14, wherein rotating the sealing member includes sliding an edge of the sealing member along a surface of the proximal ring member.

* * * * *

UNITED STATES PATENT AND TRADEMARK OFFICE
CERTIFICATE OF CORRECTION

Page 1 of 1

PATENT NO. : 10,405,883 B2
APPLICATION NO. : 15/658200
DATED : September 10, 2019
INVENTOR(S) : John Butler et al.

It is certified that error appears in the above-identified patent and that said Letters Patent is hereby corrected as shown below:

In the Claims

In Claim 2, at Column 9, Line 4, replace "at least at least" with --at least--.

Signed and Sealed this
Twenty-fourth Day of March, 2020

Andrei Iancu
*Director of the United States Patent and Trademark Office*